US012565644B2

(12) United States Patent
Haesendonckx

(10) Patent No.: US 12,565,644 B2
(45) Date of Patent: Mar. 3, 2026

(54) NUCLEIC ACID PURIFICATION CHEMISTRY

(71) Applicant: Biocartis NV, Mechelen (BE)

(72) Inventor: Max Haesendonckx, Mechelen (BE)

(73) Assignee: Biocartis NV, Mechelen (BE)

( * ) Notice: Subject to any disclaimer, the term of this patent is extended or adjusted under 35 U.S.C. 154(b) by 935 days.

(21) Appl. No.: 17/633,408

(22) PCT Filed: Aug. 7, 2020

(86) PCT No.: PCT/EP2020/072225
§ 371 (c)(1),
(2) Date: Feb. 7, 2022

(87) PCT Pub. No.: WO2021/023854
PCT Pub. Date: Feb. 11, 2021

(65) Prior Publication Data
US 2023/0399633 A1      Dec. 14, 2023

(30) Foreign Application Priority Data
Aug. 8, 2019      (EP) ...................................... 19190647

(51) Int. Cl.
*C12N 15/10*           (2006.01)

(52) U.S. Cl.
CPC ................................ *C12N 15/1006* (2013.01)

(58) Field of Classification Search
CPC .................................................. C12N 15/1006
USPC ....................................................... 536/25.42
See application file for complete search history.

(56) References Cited

U.S. PATENT DOCUMENTS

| | | | | |
|---|---|---|---|---|
| 2,010,015 A | * | 8/1935 | Fletcher .................... | D21J 1/08 |
| | | | | 428/537.7 |
| 5,610,287 A | * | 3/1997 | Nikiforov ............ | C12Q 1/6834 |
| | | | | 536/24.31 |
| 7,932,551 B2 | | 4/2011 | Kim et al. | |
| 2002/0103350 A1 | | 8/2002 | Lyles | |
| 2005/0009036 A1 | * | 1/2005 | Montesclaros .... | C12N 15/1006 |
| | | | | 435/270 |

FOREIGN PATENT DOCUMENTS

| | | | |
|---|---|---|---|
| EP | 389063 | A2 | 9/1990 |
| EP | 1896180 | A2 | 3/2008 |
| EP | 1904234 | A1 | 4/2008 |
| EP | 198351 | A2 | 10/2008 |
| EP | 2419705 | A1 | 2/2012 |
| WO | 9515970 | A1 | 6/1995 |
| WO | 2007004103 | A1 | 1/2007 |
| WO | 2010015835 | A1 | 2/2011 |
| WO | 2015165859 | A1 | 11/2015 |
| WO | 2016073824 | A1 | 5/2016 |
| WO | 2018156906 | A1 | 8/2018 |

OTHER PUBLICATIONS

Boom, R. et al. "Rapid and Simple Method for Purification of Nucleic Acids". Journal of Clinical Microbiology, vol. 28, No. 3, 495-503, (Mar. 1990).
Hourfar, M. et al. "High-Throughput Purification of Viral RNA Based on Novel Aqueous Chemistry for Nucleic Acid Isolation". Clinical Chemistry, 51:7, 1217-1222, (2005).
Melzak, K. et al. "Driving Forces for DNA Adsorption to Silica in Perchlorate Solutions". vol. 181, Issue 2, Aug. 10, 1996, pp. 635-644.
J. M. Orosz and J. G. Wetmur. "DNA melting temperatures and renaturation rates in concentrated alkylammonium salt solutions". Biopolymers, vol. 16, 1183-1199, 1977.
Meek et al. "Enzymes adsorbed on an ion exchanger as a post-col. reactor: application to acetylcholine measurement" (1984 J.Chrom. 317: 343-347).
Unceta et al. "Simultaneous determination of citalopram, fluoxetine and their main metabolites in human urine samples by solid-phase microextraction coupled with high-performance liquid chromatography" (2008 J.Pharm. Biom.Anal. 46:763-770).

* cited by examiner

*Primary Examiner* — Yih-Horng Shiao
(74) *Attorney, Agent, or Firm* — Quarles & Brady, LLP

(57) ABSTRACT

The present invention generally relates to the field of nucleic acid isolation on silica solid support. In particular, a novel silica-solid support nucleic acid binding buffer chemistry is hereby disclosed, which is based on the use of a small quaternary organic compounds, e.g. tetramethylammonium chloride (TMAC), at acidic conditions. This novel nucleic acid purification chemistry purifies not only RNA but also DNA and has the potential for being implementable in a wide variety of commercial kits ranging from the spin columns to integrated Lab-On-A-Chip (LOC) devices such as disposable cartridges that make use of a solid-phase extraction technology. Furthermore, the present methods may be performed using relatively small volumes of binding buffer and consequently in such integrated or closed molecular diagnostic devices, they have the potential of allowing increased volumes of sample input, which for liquid biopsy samples such as plasma or urine, can enhance the chances of detecting rare nucleic acid targets.

17 Claims, 15 Drawing Sheets

NUCLEIC ACID PURIFICATION CHEMISTRY

CROSS-REFERENCE TO RELATED APPLICATIONS

This application is the U.S. National Stage of PCT/EP2020/072225, having international filing date of Aug. 7, 2020, and published as WO 2021/023854, which claims priority to EP 19190647.8 filed Aug. 8, 2019. The entire content of each of the above applications is incorporated herein by reference.

TECHNICAL FIELD

The present invention generally relates to the field of nucleic acid isolation on silica solid support. In particular, a novel silica-solid support nucleic acid binding buffer chemistry is hereby disclosed, which is based on the use of a small quaternary organic compounds, e. g. tetramethylammonium chloride (TMAC), at acidic conditions. This novel nucleic acid purification chemistry purifies not only RNA but also DNA and has the potential for being implementable in a wide variety of commercial kits ranging from the spin columns to integrated Lab-On-A-Chip (LOC) devices such as disposable cartridges that make use of a solid-phase extraction technology. Furthermore, the present methods may be performed using relatively small volumes of binding buffer and consequently in such integrated or closed molecular diagnostic devices, they have the potential of allowing increased volumes of sample input, which for liquid biopsy samples such as plasma or urine, can enhance the chances of detecting rare nucleic acid targets.

BACKGROUND

In a patent EP389063 filed in 1990, Boom et al. described a universal solid support-adsorption based nucleic acid purification technology. The Boom extraction mediates binding of nucleic acids to silica using large amounts of chaotropic salts with or without the presence of alcohols. Due to its high performance allowing nucleic acid extraction yields of >50% from biological samples, it has quickly become the golden standard in nucleic acid isolation that to date continues to be widely used in in numerous commercially available extraction kits and integrated molecular diagnostic devices. For example, the Boom protocol or slight variants thereof form the basis of DNA extraction principle used in QIAGEN's QIAamp Circulating Nucleic Acid kit or in the integrated cartridges of Biocartis NV such as Idylla ctRAS.

Due to the need of using large amounts of chaotropic salts, and later also additional alcohol, the Boom protocol requires large amounts of binding buffer relative to the amount of the biological sample. For this reason, in view of the ongoing emergence of ever-more miniaturized handheld, fully integrated, lab-on-a-chip (LOC) molecular testing devices, which frequently aim to maximize on sample volumes and consequently lack sufficient storage for buffer volumes, there exist a need for finding efficient alternatives to the Boom protocol. Another reason is that chaotropic salts are expensive, have strong PCR-inhibitory properties, and can introduce multiple challenges to the final product manufacturing line. Due to all of the above, there currently exist a need for an efficient and chaotrope free nucleic acid purification chemistry that enables increasing sample input in integrated systems, in particular for the application in the field of liquid biopsies, where sample size is becoming increasingly important for the detection of very scarce per e. g. milliliter of plasma cell-free (cf) DNA targets.

To date, there have been several attempts to develop novel chaotrope-free silica based nucleic acid purification chemistries. Notable examples of them include:

A method published by Hourfar et al. in 2005, describing the purification of viral RNA based on the use of acidic conditions and kosmotropic salt. The publication is entitled "High-Throughput Purification of Viral RNA Based on Novel Aqueous Chemistry for Nucleic Acid Isolation". The method isRNA-specific and is not suitable for DNA purification from plasma.

A similar method was published by Lee et al. in 2008, which involves isolation of total RNA from *E. coli* by using kosmotropic Hofmeister salts. Additionally, Lee et al. hold a patent U.S. Pat. No. 7,923,551, entitled "Method of purifying RNA using kosmotropic salt". Both the publication and the patent describe and focus on an RNA-selective purification chemistry based on the use of acidic conditions and kosmotropic salt, however do not provide any teachings on how to apply this chemistry to DNA.

The Johns Hopkins University has a patent application WO2016/073824 entitled "Chaotrope and volatile-free method for purifying nucleic acids from plasma. The method described therein is very similar to the one in Lee at al. and includes the use of acidic conditions and kosmotropic salts to mediate the binding of RNA to silica.

MiDiagnostics holds a very similar patent application WO 2018/156906 A1 entitled "System and method for purifying and amplifying nucleic acids". The patent application describes a nucleic acid purification chemistry, which uses acidic conditions and kosmotropic salt to mediate the binding of viral nucleic acids to silica. The method however does not provide any proof it is at least as efficient as the Boom protocol nor that could be applicable to the purification of cfDNA present in plasma.

Despite being widely used in molecular diagnostics, the nucleic acid interaction with silica is still poorly understood. In fact, not much has changed since Boom et al. published the first silica-based nucleic acid purification technology in 1990. To this day, studies attempting to unravel the basic mechanics of DNA/RNA adsorption to silica are extremely limited.

Melzak et al. (1996) are one of the few that have attempted to demystify the basic mechanics of the Boom extraction technology. They have described three effects that are thought to be dominant contributors to nucleic acid adsorption to silica, which include shielded intermolecular electrostatic forces de-hydration of the DNA and silica surface intermolecular hydrogen bond formation in the nucleic acid-silica contact layer (described as the least dominant contributor).

The above-three factors can be modulated in the presence of silica solid support by addition of different salts to the nucleic acid solution. Salts have been classified by Hofmeister based on their ability to affect the structure of macromolecules, mainly proteins, in aqueous solutions. According to this classification, chaotropic salts were originally described as structure breakers, as they increase the solubility of proteins (so called "salting-in"). Contrary to the above, kosmotropic salts were described as structure makers, as they reduce the solubility of proteins (called "salting-out"). In the context of silica-based nucleic acid isolation, chaotropic salts are the natural choice due to their ability to impact water structure and cause a de-hydrating effect. In that perspective, chaotropic ions have been described by Hofmeister as large singly charged ions with low charge density, exhibiting weaker interactions with water than water with itself. They are believed to interfere little with the hydrogen bonding of the surrounding water. For example, in the original nucleic acid purification chemistry as described by Boom et al. in 1990, highly concentrated guanidinium thiocyanate salt was used thanks to its strong chaotropic nature, its cell-lysing characteristics, and its potential to de-activate ribonucleases. Conversely, kosmotropic ions are described as small or multiple charged ions with a high charge density, thus capable of breaking water-water hydrogen bonds.

Although the guanidinium cation and the thiocyanate anion are not expected to have large hydration shells, it is believed that their excessive concentration (3M-SM) used in the Boom protocol compensates for this. It is hypothesized that thanks to this high concentration of the salt, the concentration of free water can be sufficiently reduced causing dehydration of the nucleic acids and the silica membrane. Additionally, the abundance of guanidinium cations is believed to shield the electrostatic forces between the negatively charged phosphate backbones in nucleic acids and the negatively charged silanol groups on the silica surface. Both of these effects can be hypothesized to promote the hydrophobic interaction between the bases and the siloxane bridges, thus enabling adsorption of nucleic acids to the silica membrane. The later adaptions of the original Boom protocol include the addition of alcohols in the binding buffer to further reduce the concentration of free water and enhance this dehydrating effect.

According to this modification, the silica-bound nucleic acids are subsequently washed with concentrated alcohol (often 70%-90% ethanol). The washing procedure ensures the removal of residual non-nucleic acid compounds originating from the biological sample or the binding buffer. Finally, nucleic acids are eluted with a low ionic strength solution at neutral or slightly basic pH. The elution mechanism enables direct compatibility with downstream applications such as PCR and NGS.

As explained above, Hourfar et al. were the first to publish an alternative silica-based approach for RNA purification from biological samples. The subsequent publications and/or patents from Samsung electronics, Johns Hopkins University, and MiDiagnostics are based on the same chemistry that uses acidic conditions and kosmotropic salts to mediate binding of RNA (and to a much lesser extent DNA) to silica. A possible explanation why this chemistry works with RNA can be based on the following. Silica surface silanol groups have pKa values ranging from four to eight. Lowering the pH of the binding buffer-sample mixture below those values, promotes protonation of and, therefore, eliminates the strong negative charge of the weakly acidic silanol groups. Consequently, the electrostatic charge repulsion with the negatively charged phosphate backbone of nucleic acids is severely reduced or even entirely eliminated.

Additionally, a minimal amount of kosmotropic salt (i. e. (NH4}2SO4) can be used to significantly reduce the amount of free water, thus dehydrating the nucleic acids and the silica membrane. As explained earlier, strong kosmotropic ions can have large hydration shells, trapping substantial amounts of free water. In that respect, it could be hypothesized that only a limited amount of a kosmotropic salt (400 mM-1000 mM, depending on the specific salt) would be needed to provide an effect similar to e. g. SM of guanidine thiocyanate. These effects could be used to explain the binding of the flexible RNA, and to a much lesser extent the double-stranded & thus stiffer DNA, to silica.

The bound nucleic acids are then washed with high percentage alcohol, as performed in the Boom protocol, although variations were described where washing was completely alcohol free. In said variations, washing was performed with buffers similar to the binding buffer or simplified versions thereof, i. e. acidic solutions (pH 4-7) with no or limited amounts of kosmotropic salts. It could be hypothesized that these washing procedures are largely based on the attempt to remove electrostatic charge repulsion due to protonation of the silanol groups, which prevents elution of nucleic acids. Then, the elution mechanism is similar to that of the Boom protocol.

It has to be noted that this approach has proven to be very successful in the purification of RNA (often even described as RNA-selective), while purification of double stranded DNA (dsDNA) remains to be much more challenging. The dsDNA extraction yields according to these chemistries have been shown to be 10- to 100-fold lower, which is clearly insufficient for the extraction of DNA from plasma.

Herein, we have address the shortcomings of the strong-chaotrope-free nucleic acid extraction methods by successfully employing a salt consisting of a small quaternary organic compound cation and a very weakly chaotropic and highly soluble anion. A quaternary compound is a cation consisting of a central positively charged atom with four uncharged substituents, mostly alkyl and aryl groups. These cations are permanently charged, independent of the pH of their solution. They are often described as inert cations. In particular, we have observed and demonstrated that a salt consisting of, e.g., a tetramethylammonium (TMN) cation combined with a weak chaotropic chloride (Ci−) or bromide (Br−) anion creates at acidic pH unique conditions for isolating dsDNA on a silica solid support with an efficiency matching chaotrope-based protocols such as the Boom protocol.

To our knowledge, salts consisting of a small quaternary organic compound cation and a weak chaotropic anion are not used for solid-support-based nucleic acid extraction from biological samples. Although DNA and dsRNA melting and renaturation properties were studied using similar salts by J. M. Orosz and J. G. Wetmur in 1977 (Biopolymers, vol. 16, 1183-1977), their research does not consider an option of using these salts in solid-phase nucleic acid extraction. Further, WO2015165859 describes use of a sodium salt in combination with a quaternary ammonium salt in a method for enriching nucleic acids containing a single stranded poly(A) stretch (i. e. messenger RNA, primarily) while depleting unwanted nucleic acids such as e. g. rRNA, on a solid support coated with immobilized oligo-dT capture probes. The teachings of WO2015165859 imply stringent and selective specificity to poly(A) nucleic acids and do not appear to be suitable for isolation of any other types of nucleic acids from samples such as liquid biopsies. Then, WO1995015970 discloses a hybridization solution comprising tetramethylammonium chloride ((CH3)4NCI) and a cationic detergent for immobilization of synthetic oligonucleotides to a solid surface like polystyrene. Importantly, however, WO1995015970 does not teach purification on the solid support of natural nucleic acids from a complex biological sample context, and especially not from liquid biopsy sample such as plasma. In conclusion, none of the above disclosures teaches or suggests application of small quaternary organic compound salts for nucleic acid isolation as a general alternative to the Boom protocol.

The advantages of the presented here approaches as compared to the Boom protocol are several. Firstly, the Boom protocol was originally designed to isolate long genomic and plasmid DNA/RNA. Its application in molecular diagnostics has been challenged by the highly fragmented nature of the genomic material that is typically present in plasma and FFPE samples. Short fragments of nucleic acid have naturally much less hydrophobic binding sites, thus limiting their binding efficiency to silica under the high chaotrope concentrations used in the Boom protocol. Contrary to this limitation, using the presented herein approach based on the salt composed of a quaternary cation and a mild chaotrope, we were able to isolate both short and longer dsDNA fragments. Furthermore, we have observed that the extraction efficiency of short DNA (i. e. having the length ranging from 10-300 bp) can be reduced with increased pH, while the extraction efficiency of high molecular weight DNA can be increased with increased pH, thus indicating that by varying pH values, the disclosed herein approach additionally opens a way for fine-tuning the extraction efficiency in function of the desired DNA target lengths.

The next advantage of disclosed herein methods is that the chemical composition of the binding buffers does not cause protein aggregation, which in principle allows for the processing of plasma samples without a protein digestion step. The plasma-binding buffer mixture enables smooth flow rates, which facilitates its use in microfluidic devices. Consequently, for low volume or diluted samples, the protein digestion step can be skipped when using the disclosed here methods, even though for some older plasma sample with volumes>400 µL, the incorporation of a protein digestion step can still be beneficial as an optional step to increase the final extraction yields.

Then, as noted above, LOC devices or disposable cartridges often lack sufficient storage room for the relatively large amounts of binding buffer used in the Boom protocol. Additionally, chaotropic salts are expensive, have strong PCR-inhibitory characteristics, and can introduce many issues in the manufacturing line, e. g. caused by crystallization. In contrast to this, the presented here method and binding buffers are strong chaotrope-free, cheap, and very much reduce the required binding buffer volumes per sample, thus enabling increased sample input in fully integrated molecular diagnostic devices. The latter is a big advantage for processing liquid biopsies, for example obtained from cancer patients, where the amount of tumor-derived mutant DNA copies per milliliter of plasma is very scarce and hard to detect. Last but not least, the presented here methods are generic, meaning that they enable efficient purification from different biological samples of both short and long dsDNA as well as of ssDNA and potentially also RNA.

SUMMARY

The chemistry of silica-based purification of nucleic acids has not changed much since Boom et al. have published the original method in 1990. Mostly this is due to the adequate performance of the Boom extraction technology, which provides nucleic acid extraction yields>50% from biological samples. The Boom protocol mediates binding of nucleic acids to silica by using substantial amounts of chaotropic salt and alcohol. However, in the light of the recent emergence of miniaturized integrated Lab-on-a-chip (LOC) devices, there appeared a need for minimizing buffer volume contained therein in order to maximize the sample volume input they may accept. Consequently, there exists a clear need for a novel nucleic acid purification chemistry that is free from strong-chaotropes, economical, and enables increased sample input in integrated systems.

Herein, we present a novel purification chemistry that mediates binding of nucleic acids to silica by using nothing more than acidic conditions and a relatively small amount of salt composed of a quaternary ammonium compound. The disclosed methods substantially reduce the binding buffer volume relative to the sample volume, thus enabling an increased sample input, which is highly beneficial in fully integrated molecular diagnostic devices. Furthermore, the disclosed isolation methods provide an adequate nucleic acid yield that is comparable to the performance of strong chaotrope-based protocols such as the Boom protocol.

BRIEF DESCRIPTION OF FIGURES

For a fuller understanding of the presented herein concepts, reference is made to the following detailed description taken in conjunction with the accompanying drawings in which.

DETAILED DESCRIPTION

Figure 1:
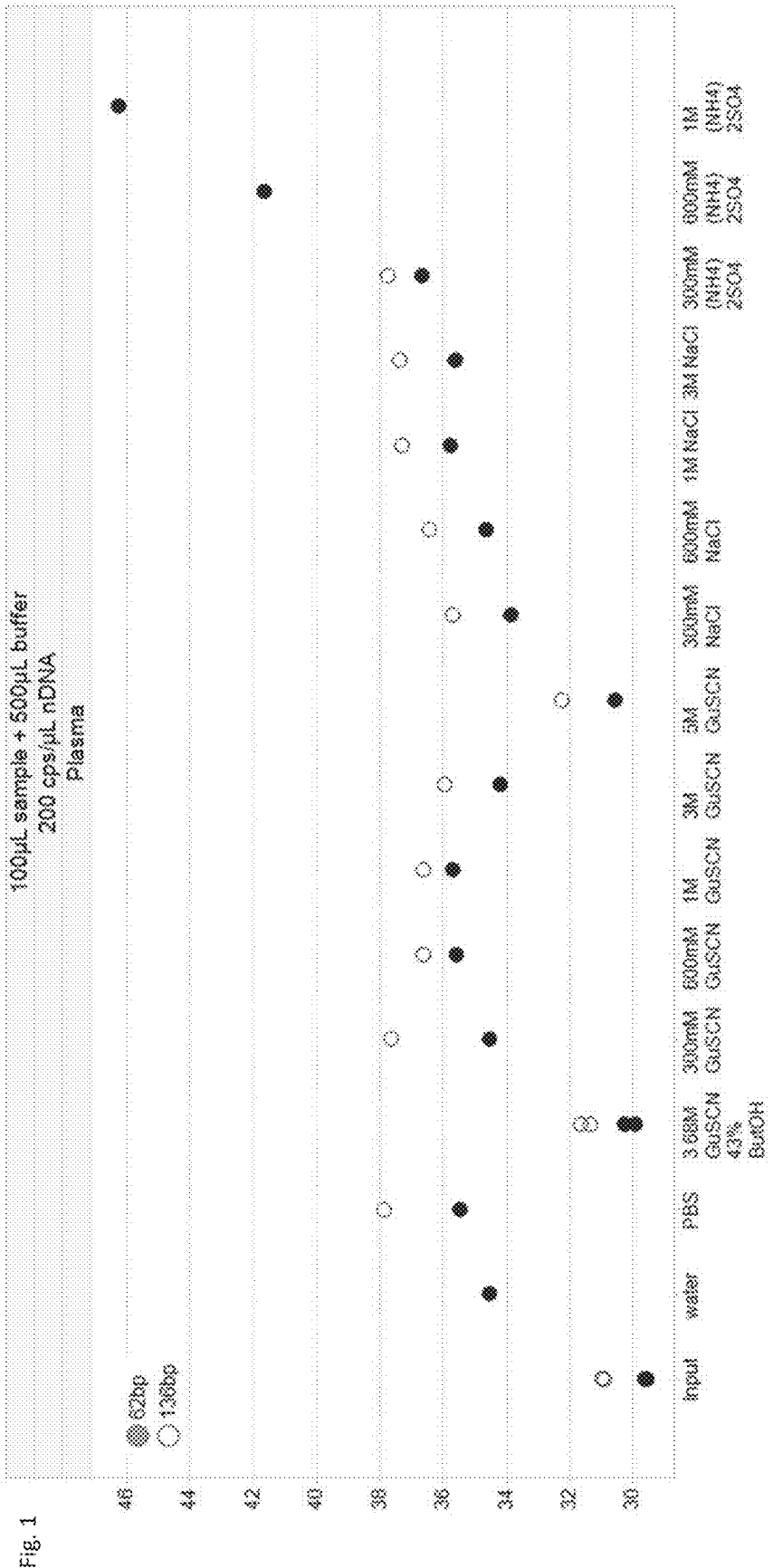
FIG. 1: shows extraction efficiencies of dsDNA in different chaotropic- and kosmotropic-salt binding buffers at neutral pH.

The present disclosure generally concerns a nucleic acid extraction method comprising contacting a biological sample, possibly being a liquid biopsy sample, with a silica solid support at pH value between 3 and 6 and in the presence of a salt consisting of:—a small quaternary organic compound, defined as a quaternary compound consisting of a central positively charged atom with four organic substituents R1-R4, wherein the number of carbon atoms in each organic substituent R1-R4 does not exceed 2; and of a bromide or a chloride anion.

In other words, a novel binding buffer chemistry is hereby disclosed, based on the use of acidic conditions and a minimal amount of salt comprising a small quaternary organic compound, which provides a generic, chaotrope-free nucleic acid purification protocol that enables the efficient isolation of not only RNA but also DNA. As used herein, the term "quaternary compound" is to be used interchangeably with the term "quaternary organic compound", which is to be understood as a chemical compound defined as being or having a ion being a cation consisting of a central positively charged atom with four organic substituents (i. e. alkyl and/or aryl groups and discounting hydrogen atoms), further designated as organic substituents R1-R4. As used herein, the term "small quaternary organic compound" is to be understood as such quaternary organic compound wherein the number of carbon atoms in each one of the four organic substituents R1-R4 does not exceed two carbon atoms. For solubility considerations, a preferred organic substituent is a single carbon group, i. e. methyl group. We consider that the more of the four organic substituents Ri-R4 consist of a methyl group, the better soluble, and thus easier and more preferred to work with the small quaternary organic compound will be. Despite the above, we also believe that organic substituents comprising two carbon atoms at one or more of the four organic substituents Ri-R4, are still sufficiently soluble and decently suitable for performing the disclosed herein methods.

The best-known quaternary compounds are quaternary ammonium salts, which are salts comprising a quaternary ammonium cation having a nitrogen atom at the center (R4W). Hence, in an embodiment, a method is provided, wherein the positively charged atom of the small quaternary organic compound is nitrogen. Other possible examples and plausibly workable embodiments may include quaternary phosphonium salts (R4P+), quaternary arsonium salts (R4As+) like arsenobetaine, as well as some arsenic-containing superconductors. Substituted stibonium (R4Sb+) and bismuthonium salts (R4Bi+) have also been described to exist and may possibly work in certain embodiments of the presented herein methods.

IAs demonstrated later in the examples, also the anion of the salt as used in the present methods impacts the final nucleic acid extraction yields. Contrary to the above-described known RNA specific methods, strongly kosmotropic anions do not seem to be suitable for the extraction of DNA. Instead, we have realized that a very week chaotropic ion like bromide or the even weaker chaotrope/borderline kosmotrope chloride generally provide the best results, with a slight preference for the latter in most of the experimental settings. Thus, in a next embodiment, a method is provided wherein the anion is chloride.

We hypothesize that the above highlighted differences between RNA and DNA binding to silica may possibly stem from the at least partially single-stranded nature of RNA. Namely, we think that the binding of RNA to silica is easier than the binding of dsDNA, which may possibly be due to the increased rotational mobility of the bases in the single-stranded nucleic acids, thus increasing the amount of their available hydrophobic binding sites. Conversely, the double stranded DNA could possibly require substantial changes to its helical structure to promote hydrophobic interaction between the bases and the siloxane (Si-0-Si) bridges of the silica membrane.

It is believed that the DNA double helix is mainly stabilized by:
 hydrogen bonding between the bases and the aqueous environment; electrostatic shielding of the negatively charged phosphate backbones;
 base stacking interactions between adjacent bases.

The latter has been described as the most dominant contributor to double helix stability. We have hypostasized that destabilization of the double helix is required to allow for efficient binding to the silica membrane and that the type and amount of ions present have a major role in defining the helical conformation of double stranded DNA.

From our experience, acidic conditions and kosmotropic salts do not appear to facilitate the binding of dsDNA to silica. It is possible that the use of a limited amount of kosmotropic salt will alter the conformation of the double helix, possibly further reducing the affinity of dsDNA to the silica membrane. For this reason, we hypothesize, that kosmotrope-based methods as known before the present approach are RNA-selective. Small cations with a high charge density are theoretically capable of fitting between the minor and major grooves of the helical structure, while strong kosmotropic anions may strongly dehydrate the double helix, possibly causing conformational change of the double helix to stiff A-DNA, thus hypothetically resulting in reduced availability of the bases to bind to the silica solid support. Following this reasoning, we have hypothesized that to counteract this affinity reducing effect and facilitate the binding of dsDNA to the silica membrane, the stabilizing effect of the cation should be eliminated and the dehydrating effect of the kosmotropic anion should be reduced. We have found that this effect can be achieved by using a salt composed of a quaternary ammonium compound and a weak chaotropic/weak kosmotropic anion such as chloride, which has been described to be on the borderline of chaotropic and kosmotropic behavior. A quaternary ammonium compound is a cation consisting of a central positively charged nitrogen atom with four uncharged substituents, mostly alkyl and aryl groups. These cations are permanently charged, independently of the pH of their solution. They are often described as inert cations.

Based on our theoretical model, we hypothesized that the success of the present approach using a small quaternary organic compound like TMAC, may at least partially result from the prevention of electrostatic shielding of the negatively charged dsDNA phosphate backbone by the inertness and sheer size of the quaternary ammonium cation. It is also possible that the methyl groups of TMA+cause steric hindrance, thus preventing its binding to the minor or major groove of the helical structure. By using a salt composed of such an inert cation, we think that the conformational shift negatively affecting dsDNA affinity to silica is prevented, while the weak chaotropic anion may be still providing sufficient dehydration of the silica support for the efficient binding of the dsDNA double helix, which we observe.

In line with the above, in a next embodiment, a method is provided wherein the small quaternary organic compound is tetramethylammonium chloride, further referred to as TMAC. In further embodiments, as it is supported in the examples below, the concentration of the small quaternary organic compound, as exemplified as TMAC concentrations under silica binding conditions, is comprised between 0.1 M-2 M, possibly between 0.5 M-1.8 M, or possibly between 0.8 M-1.6 M, or possibly between 1 M-1.4 M, or can be about 1.2 M.

One of the advantages of the disclosed methods is, depending on the desired application, their potential maximizing of the sample input volumes vs the required volume of the binding buffer. This feature is particularly advantageous for integrated devices such as closed fluid cartridges, which have a defined and limited inner volume. The feature directly depends on the solubility of the components of the binding buffer. The preferred small quaternary organic compound TMAC has an excellent solubility of >1000 g/L, which corresponds to obtaining a stable at room temperature solution of 9M TMAC. Sodium acetate, being an exemplary buffering compound for ensuring acidic pH conditions, also has a high solubility in water equal to 5.6 M. Hence, for example, if in an embodiment of the disclosed methods 1.2 M TMAC and 0.2 M acetate are used at the conditions of nucleic acid binding to silica (i. e. conditions at which the sample and the binding buffer are contacted with the silica solid support), a 6/1 sample to buffer ratio is possible to be achieved at the binding conditions. Such exemplary binding buffer would comprise 8.4 M TMAC and 1.4 M acetate, both of which concentrations are soluble at room temperature. Thus, in possible embodiments, the sample/buffer ratios could range all the way from 6/1 to 1/6, depending on what suits the application.

The uniqueness of the disclosed approach lies within the use of a salt composed of a small quaternary organic compound and weak chaotropic anion (i. e. chloride, or to certain extent also bromide) to mediate the binding of nucleic acids (not only RNA but notably also DNA, dsDNA in particular) to a silica membrane in acidic conditions. As used herein, the term "acidic conditions" is to be understood as referring to conditions in an aqueous solution wherein the pH value, as broadly accepted in the art and estimated on a standard pH base 10 logarithmic scale of the molar concentration (measured in units of moles per liter) of hydrogen ions, is at least below the value of 7. Consequently, in a further embodiment a method is provided, wherein the pH value is comprised between 4 5.8; 4.2-5.6; 4.4-5.4; 4.6-5.2; and possibly is about 5. We believe that the provision of the above-described specific salt compositions at these pH ranges and in presence of a silica solid binding support provides a generic nucleic acid purification technology compatible not only with RNA but, importantly, also DNA.

Following the biding to silica, the nucleic acids can then be washed and eluted by standard silica wash and elution methods as known in the art.

For example, washing of the bound nucleic acids can be performed in a mode similar to the methodology used in the original Boom protocol. I.e., a concentrated alcohol, often 90% ethanol, can be used. As discussed before, some of the previously known methods described washing procedures based on acidic solutions with no to minimal amounts of kosmotropic salt. Based on our observations, we believe that such an approach is solely compatible with RNA applications. We think that rehydration of dsDNA during washing will cause stabilization of the double helix due to hydrogen bond formation between the bases, resulting in its premature release from the silica solid support.

Then, the elution mechanism will be largely very similar to that known from the previously known methods. For example, a low ionic strength solution at neutral or slightly basic pH is used. This can be either water, or a regular PCR buffer. We also have observed that the pH and the amount of divalent cations in the elution buffer can substantially influence elution efficiency. This is possibly because the charge repulsion between the negatively charged silanol groups and the negatively charged phosphate backbone is likely plays a substantial role during the elution. Hence, deprotonation (strengthening of the negative charge) of the silanol groups by increasing the pH of the elution buffer will result in increased elution efficiency. The complete absence of small and/or divalent cations also promotes elution efficiency possibly due to the lack of electrostatic shielding. These mechanisms are generally known in the field, and therefore the choice of a protocol-appropriate wash and elution strategy will constitute no major problem to a skilled person and, consequently, will not be discussed here further.

In alternative further embodiments, as for at least some types of biological samples, the abandoning of the strong chaotropic chemistry of the Boom protocol may introduce several challenges, several additions to the presently disclosed methods can be introduced.

In particular, when focusing on the Boom-extraction-based protocols, the chaotropic salts allow to:
  (i) prevent other biomolecules (e. g. proteins, lipoproteins) from precipitating on the silica solid support;
  (ii) inhibit the activity of nucleases;
  (iii) release DNA from histone proteins in order to enhance interaction with silica. As it will be known by those skilled in the art, the same effects can be achieved by an introduction of a protease for performing a protein digestion step, which can be advantageous in in particularly difficult (e. g. old) samples. Therefore, in another embodiment, the method is preceded by a protease treatment, for example with proteinase K.

In another embodiment, a method is provided wherein the biological sample is a liquid biopsy sample. As used herein, the term "liquid biopsy" or a "liquid biopsy sample" shall be understood as referring to any non-tissue specimen, especially body fluid sample, obtained from a subject. Liquid biopsy sources include but are not limited to blood, plasma, serum, urine, cerebrospinal (CSF) fluid, amniotic fluid, other body fluids such as saliva, sweat, tears, breast milk, semen, stool, pleural fluid, peritoneal fluid or washings etc. Analyzing nucleic acids in liquid biopsy samples can minimize the need for expensive, invasive, and frequently painful tissue and/or tumor biopsies to enable dynamic disease or other physiological state monitoring. For example, in cancer patients, cell-free tumor DNA or RNA extracted from liquid biopsies can potentially be used in detection of mutations, translocations or copy number alterations, and the expression of specific cancer markers.

Blood (plasma, serum or whole blood alike) is the most commonly described fluid used in liquid biopsy sample analysis in humans. In cancer patients, blood is the source of circulating tumor cells (CTCs), and cell-free DNA (cfDNA) and cell-free RNA (cfRNA) including circulating tumor DNA (ctDNA) and circulating tumor RNA (ctRNA), respectively, released by tumor tissues, which can be used to detect mutations present in the patients' tumors. Of note, ctDNA comprises however only a tiny fraction of cfDNA present in the blood, which highlights the importance of maximizing sample volumes for nucleic acid analyses in order to detect rare mutations. Furthermore, cfDNA is always of low quality and fragmented to the approximate size of a nucleosome (140 bp). Consequently, for certain cancer types, including kidney, prostate, and upper and lower tract urothelial carcinomas, alternative liquid biopsy approaches using as urine may be a richer source of tumor-derived material. Urine also has other unique benefits such as ease of acquisition (does not require trained medical staff), lack of patient discomfort (increased patient compliance), and may have fewer contaminating proteins compared to blood. Urine, however, still is a very diluted material and consequently its use in diagnostic approaches, especially on PoC devices, would also benefit from maximization of sample input volumes. In view of the currently existing need for nucleic acid extraction chemistries that allow maximizing blood or urine sample volume inputs, especially inside of integrated PoC devices like fluidic cartridges, and because present methods are very much suited for this purpose, in another exemplary embodiment, a method is provided wherein the liquid biopsy sample is selected from plasma, serum, whole blood, or urine.

In a related embodiment, a method is provided wherein the nucleic acid is DNA which despite being relatively diluted in liquid biopsy samples, is more stable than RNA, and can be isolated using the disclosed herein methods at efficiencies similar to the ones of Boom-extraction-based protocols In a further embodiment, the DNA can be cell free DNA (cfDNA) or circulating tumor DNA (ctDNA), which usually are fragmented and/or double stranded DNA types.

Of note, for certain whole blood or old plasma or serum samples, we have observed that the presented herein novel binding chemistry (e. g. involving 1 M TMAC+0.2M acetate at pH 5) could sometimes become challenged likely due to excessive protein precipitation and/or blocking of the silica solid support, which may result in reduced extraction yields. Depending on the sample type, this issue can be addressed by an addition of an appropriate detergent. Consequently, in another alternative embodiment, a method is provided wherein the contacting happens in the presence of a detergent. As used herein, the term "detergent" is to be construed in a broad sense as relating to chemical compounds or mixtures having surfactant properties. As used herein, the term "detergent" is to be understood as synonymous to the term "surfactant", relating to any compound or to a mixture of compounds having amphiphilic properties and lowering surface tension of a liquid comprising them. We also believe that detergents may further assist the efficiency of the process by additionally enhancing the removal of DNA from histones and in inhibition of nuclease activity.

In a particular embodiment, for example in the context of a sample being a plasma sample that may potentially show issues stemming from an abundant presence of albumin, a method is provided wherein the detergent is a quaternary ammonium compound detergent. We have observed that quaternary ammonium compound detergents, such as cetyltrimethylammonium bromide (CTAB), strongly promote the solubility of albumin, preventing it from saturating the silica membrane. The quaternary nature of such detergents possibly also prevents them from altering the helical conformation of DNA, thus they may be advantageous by hypothetically not excreting any impact on the binding efficiency of dsDNA to silica. During our experiments using difficult plasma samples we have appreciated the effects obtained with CTAB, notably due to its observed efficacy at even very low silica binding concentration ranges between 0.25% and 1%. Such low concentrations are interesting for closed integrated device applications, wherein maximizing sample input volume happens at the expense of minimizing the buffer volume. Consequently, in another embodiment, a method is provided wherein the quaternary ammonium compound detergent is cetyltrimethylammoniumbromide (CTAB).

In another embodiment, the method is performed inside of a fluidic cartridge, possibly being a closed fluidic cartridge, likely forming part of an automated system. In an embodiment of the above embodiment, the cartridge can be of the type that directly accepts a biological sample, obtains a PCR grade nucleic acid from it using the presented herein novel nucleic extraction chemistry, and is suitable and adapted to house at least one PCR reaction.

As used herein, the term "cartridge" is to be understood as a self-contained assembly of chambers and/or channels, which is formed as a single object that can be transferred or moved as one fitting inside or outside of a larger instrument that is suitable for accepting or connecting to such cartridge. A cartridge and its instrument can be seen as forming an automated system or an automated platform. Some parts contained in the cartridge may be firmly connected whereas others may be flexibly connected and movable with respect to other components of the cartridge. Analogously, as used herein the term "fluidic cartridge" shall be understood as a cartridge including at least one chamber or channel suitable for treating, processing, discharging, or analyzing a fluid, likely a liquid. An example of such cartridge is given in WO2007004103. Advantageously, a fluidic cartridge can be a microfluidic cartridge. In the context of fluidic cartridges the terms "downstream" and "upstream" can be defined as relating to the direction in which fluids flow in such cartridge. Namely, a section of a fluidic path in a cartridge from which a fluid flows towards a second section in the same cartridge is to be interpreted as positioned upstream of the latter. Analogously, the section to which a fluid arrives later is positioned downstream with respect to a section which said fluid passed earlier. In general, as used herein the terms "fluidic" or sometimes "microfluidic" refers to systems and arrangements dealing with the behavior, control, and manipulation of fluids that are geometrically constrained to a small, typically sub-millimeter-scale in at least one or two dimensions (e. g. width and height or a channel). Such small-volume fluids are moved, mixed, separated or otherwise processed at micro scale requiring small size and low energy consumption. Microfluidic systems include structures such as micro pneumatic systems (pressure sources, liquid pumps, micro valves, etc.) and microfluidic structures for the handling of micro, nano- and picoliter volumes (microfluidic channels, etc.). Exemplary fluidic systems were described in EP1896180, EP1904234, and EP2419705 and can accordingly be applied in certain embodiments as disclosed herein. In line with the above, the term "chamber" is to be understood as any functionally defined compartment of any geometrical shape within a fluidic or microfluidic assembly, defined by at least one wall and comprising the means necessary for performing the function which is attributed to this compartment. Along these lines, "amplification chamber" is to be understood as a compartment within a (micro)fluidic assembly, which suitable for performing and purposefully provided in said assembly in order to perform amplification of nucleic acids. Examples of an amplification chamber include a PCR chamber and a qPCR chamber.

As used herein, the term "automated system" is to refer to integrated platform comprising an instrument and disposable material, such as plastics and solutions, which the system uses in an automated manner to complete a certain process. Such process can be initiated by a user but throughout its automated processing within the system, the user's intervention is not necessary until the process completion. As used herein the term "instrument" is to be understood as a machine equipped with at least a user interface (e. g. comprising at least a start button or an electricity plug), an onboard computer with software, and programmed to perform certain functions like run an assay, which can e. g. involve mixing, sonication, heating, data detection and collection, and possibly analysisetc. In a possible embodiment, the interface can be in a form of a console comprising a computer system running user interface software capable of initiating tests, displaying test results, and communicating with external information systems. An excellent automated system capable of readily accommodating the present methods is a diagnostic platform Ldylla™ manufactured by Biocartis NV, which uses a disposable reagent-bearing cartridge that is engageable with a cartridge-processing instrument and provides sample-to-result analytical performance.

In alternative embodiments, further provided are products directly related and/or enabling performing of the methods as described above. In a simplest embodiment of such product, a binding buffer solution is provided comprising a buffering agent (e. g. acetate) adapted to keeping pH at a value between 3 and 6 and further comprising TMAC, both at concentrations directly adapted to obtain the desired concentrations at silica solid support binding conditions after mixing with a sample of choice. Advantageous examples of such binding buffer solutions include e. g. 2.33 M TMAC and 0.47 M acetate, 3.6 M TMAC and 0.6M acetate, 4.8 M TMAC and 0.8 M acetate, 6 M TMAC and 1 M acetate, 7.2 M TMAC and 1.2 M acetate, 8.4 M TMAC and 1.4 M acetate.

In alternative embodiments of the above embodiment, binding buffer solution is provided further comprising a quaternary ammonium compound detergent and/or a proteinase K, at appropriate concentrations as explained above. Using the examples of the above listed solutions, CTAB concentrations could be 2.33 M TMAC and 0.47 M acetate and 1.17% (w/v) CTAB, 3.6 M TMAC and 0.6 M acetate and 1.5% (w/v) CTAB.

In alternative embodiments of the disclosed herein products, a kit and/or a fluidic cartridge could be provided comprising any of the above described binding buffer solutions. As used herein, the term "kit" is to be interpreted as a set of objects comprising at least one article or an assembly or articles or equipment needed for a specific purpose, like performing a molecular biology process or an assay. A kit may be provided in a form of a standard benchtop nucleic acid purification kit comprising containers with reagents like the binding buffer, wash buffers, etc. and e. g. one or more silica solid support spin columns, membranes, beads, or the like. Alternatively, the kit may comprise a cartridge or simply be provided in a form of a cartridge. Along these lines, in a further embodiment, a cartridge is provided, said cartridge comprising a binding buffer solution a buffering agent adapted to keeping pH at a value between 3 and 6 and further comprising TMAC. In a further embodiment, the binding buffer solution within such cartridge could further comprise CTAB. In another embodiment, such cartridges could advantageously further house or comprise silica solid support for nucleic acid purification. In further possible embodiments, such cartridges could be fluidic cartridges and/or could be adapted for processing liquid biopsy samples, such as e. g. plasma or urine.

Lastly, also provided here are uses of the described herein methods and products (such as kits, cartridges, automated systems etc. for the extraction of nucleic acids from liquid biopsy samples. In further embodiments, uses are provided of the disclosed methods and products for the extraction of DNA, likely being double stranded DNA (dsDNA), possibly being cell free DNA (cfDNA) or even circulating tumor DNA (ctDNA).

The presently described novel nucleic acid purification chemistry and related to it products have the potential of being applied into a wide variety of commercial kits, Lab-On-A-Chip (LOC) devices or disposable cartridges that make use of a solid-phase extraction technology to isolate nucleic acids from biological samples. More specifically, its application in fully integrated molecular diagnostic devices could be of great value due to the relatively small volume of the required binding buffer, which enables increasing of sample input vis. the necessary buffer volumes. Working examples of the presented herein concepts are given below.

EXAMPLES

General Experimental Set-Up.

A silica spin column (Machery-Nagel, blood column nucleospin) was mounted on the QIAvac 24 plus system, being a vacuum manifold that is connected to a vacuum pump by the QIAvac connecting system. The complete set-up can be used as a flow-through system. A plasma sample was mixed with binding buffer solutions according to a 4/3 ratio (e. g. 1 mL of plasma and 0.75 mL of binding buffer) and run over the silica spin column. Thus, the binding buffer was generally diluted 2.33× times when mixed with plasma. The 4/3 ratio is not a requirement, but merely an arbitrary choice, partly related to the design of the ldylla cartridge (the lysis chamber allows for a maximal input of 7 mL), even though this is a silica spin column experiment. It is definitely possible to further increase the concentration of the binding buffer and thus reduce the required buffer volume in relation to the sample volume. However, for this specific spin column setting the 1.75-fold dilution of the plasma samples appeared satisfactory from clogging and flowrate perspectives. The silica membrane was subsequently washed with washing buffer after which the spin column was removed from the vacuum manifold. The spin column was then placed in a 1 mL Lo-Bind Eppendorf tube, and subjected to a centrifugation step of one minute at ten thousand rounds per minute (rpm). The spin column was then transferred to a new 1 mL Lo-Bind Eppendorf tube, followed by with the addition of the elution buffer. After a two-minute incubation at room temperature, the spin column was then subjected to an additional centrifugation step of one minute at ten thousand rpm. The eluted product was then analyzed by qPCR, providing a relative quantification of the purified DNA.

Sample Type and Binding Buffer Chemistry.

Plasma (Innovative research) was spiked with nucleosomal DNA (nDNA), isolated from whole blood. Spiking is useful to provide robust downstream qPCR-based target detection when processing smaller plasma volumes. Additionally, nucleosomal DNA is characterized by a fragmentation pattern that is very similar to that of cell-free DNA (cfDNA). The presence of short fragments enables us to evaluate their extraction efficiency. 100 μL of plasma was spiked with 20,000 copies of nDNA. The spiked plasma was then mixed with 500 μL of the binding buffer. The binding buffer was composed of 1.2M tetramethylammonium chloride (TMAC) dissolved in a 0.24M sodium acetate pH 5 buffer. Which results in a final concentration of 1M TMAC and 0.2M sodium acetate when mixed with the plasma sample. This acidic mixture with a total volume of 600 μL was then run over the silica spin column, as described above.

Washing Buffer Chemistry.

Washing of the silica membrane was performed by running 1000 μL of 90% ethanol over the spin column. Subsequently, any residual ethanol traces were removed by subjecting the spin columns to a centrifugation step of one minute at ten thousand rpm.

Elution Buffer Chemistry.

Elution of the DNA was performed by rehydrating the silica membrane with water or a Tris-HCl pH 8.6 buffer. It is of importance that the elution buffer is at room temperature, and is in contact with the silica membrane for a minimum of two minutes. Subsequently the spin column is subjected to a final centrifugation step (one minute, ten thousand rpm). The eluted product is then recuperated in a 1 ml Lo-Bind Eppendorf tube.

qPCR Design and Conditions.

In order to evaluate the extraction efficiency of both short and long DNA fragments, a triplex design was used that is composed of three amplicons, each with a different size. The target amplicons are 62 bp, 98 bp and 136 bp long. Differences in Ct values between the shortest and the longest amplicon indicate the presence of short target fragments. Primer and probe sequences can be provided upon request. 20 μL of the eluted product was mixed with 5 μL of PCR buffer. The components of the final PCR reaction were; 50 mM KCl, 20 mM Tris-HCl pH 8.6, 2 mM MgCb, 0.2 mM dNTP mix, 300 nM of each primer and probe and 5 units of Gotaq DNA polymerase. The qPCR reaction was performed on the Biorad CFX96 Touch™ Real-Time PCR Detection System. The total reaction volume was 25 μL. The cycling protocol included a hotstart (5' 95°) followed by 50 cycles of denaturation (3" 95°) and annealing (30" 64° C.°). The fluorescent signal was measured after each cycle.

Results

We first investigated extraction efficiencies of dsDNA in different chaotropic- and kosmotropic or mild chaotropic-salt binding buffers at neutral pH. The Ct values of PCR for 62 bp and 136 bp amplicons as extracted in the different binding buffers are shown on the Y-axis in FIG. 1. The X-axis displays different binding buffer compositions at neutral pH. 'Input' is a reference point and reflects the Ct values that are obtained when the total amount of spiked nDNA is targeted. Thus delta Ct with the reference point indicates extraction efficiency (i. e. a delta of 1 Ct=50% extraction efficiency). If the delta Ct between the small and the large amplicon remains the same as for the reference point, this indicates that there is no loss of small (62 bp-136 bp) fragments. The results illustrate that the binding efficiency of dsDNA to silica is reduced when the amount of kosmotropic salt in the binding buffer (NaCl or (NH4)2SO4) is increased at neutral pH. As explained earlier, we hypothesized that this may be due to the small kosmotropic cations (Na+ and NH4+) causing a stabilizing effect on the DNA double helix. Clearly, in neutral conditions a highly concentrated chaotropic salt is preferred to mediate the binding of DNA to the silica membrane.

Figure 2:
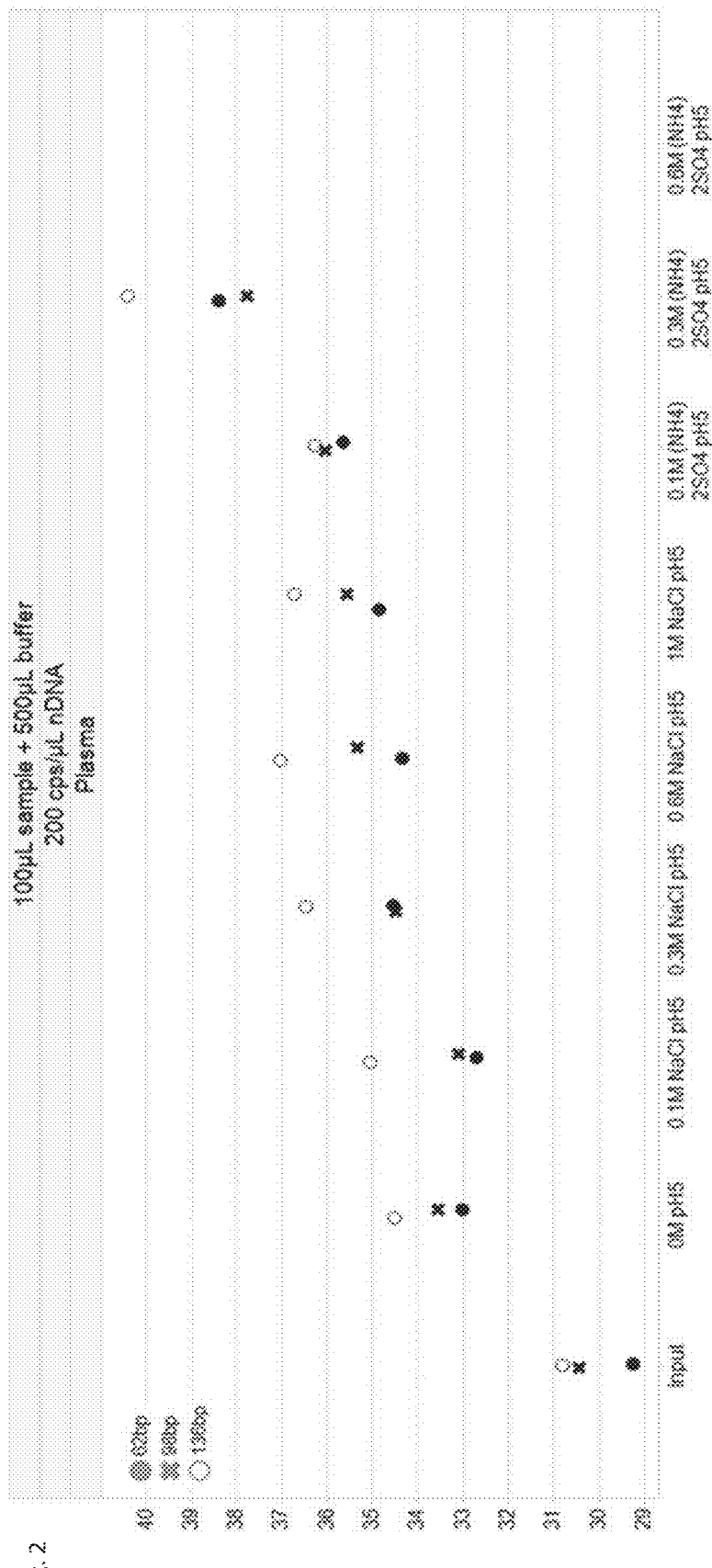
FIG. 2: shows extraction efficiencies of dsDNA in different chaotropic- and kosmotropic-salt binding buffers at acidic pH.

We then repeated the experiment using acidic conditions (pH 5). The results are shown in FIG. 2. As before, the Y-axis displays Ct values of all three different amplicon sizes, while the X-axis displays different binding buffer compositions. The data show that the use of acidic conditions (pH 5) and a kosmotropic salt, as described in the prior art, do not efficiently mediate the binding of nDNA to the silica membrane. 0.1M of NaCl at pH 5 appeared to be the best performer, with an extraction efficiency of approximately 6.25% (delta Ct=4).

Figure 3:
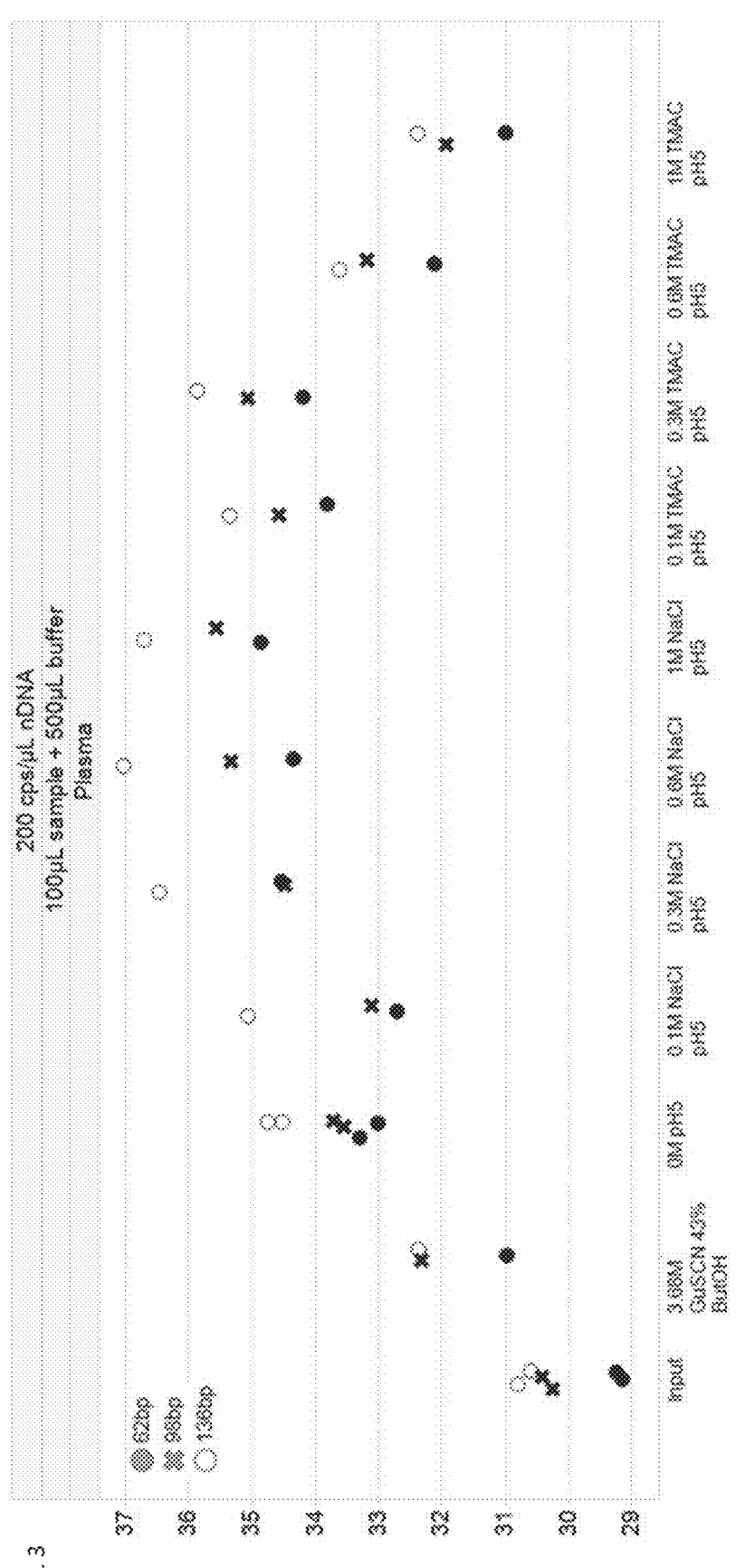
FIG. 3: shows comparison between a Boom-extraction binding buffer and chloride-based buffers with or without a quaternary ammonium compound.

We then compared the performance of a chaotropic Boom binding buffer (3.68M GuSCN and butanol) vs buffers containing chloride-based salts with or without a quaternary ammonium compound. The results are shown in FIG. 3. The Y-axis displays Ct values of all three different amplicon sizes. The X-axis displays different binding buffer compositions. The data shows that the use of a salt composed of a quaternary ammonium cation (TMA+) and a kosmotropic anion (Cl–) efficiently mediates the binding of DNA to the silica membrane. The results support the hypothesis that the inertness of the quaternary cation enables the destabilization of the helical structure of DNA, thus increasing the amount of the available silica-binding sites.

Figure 4:
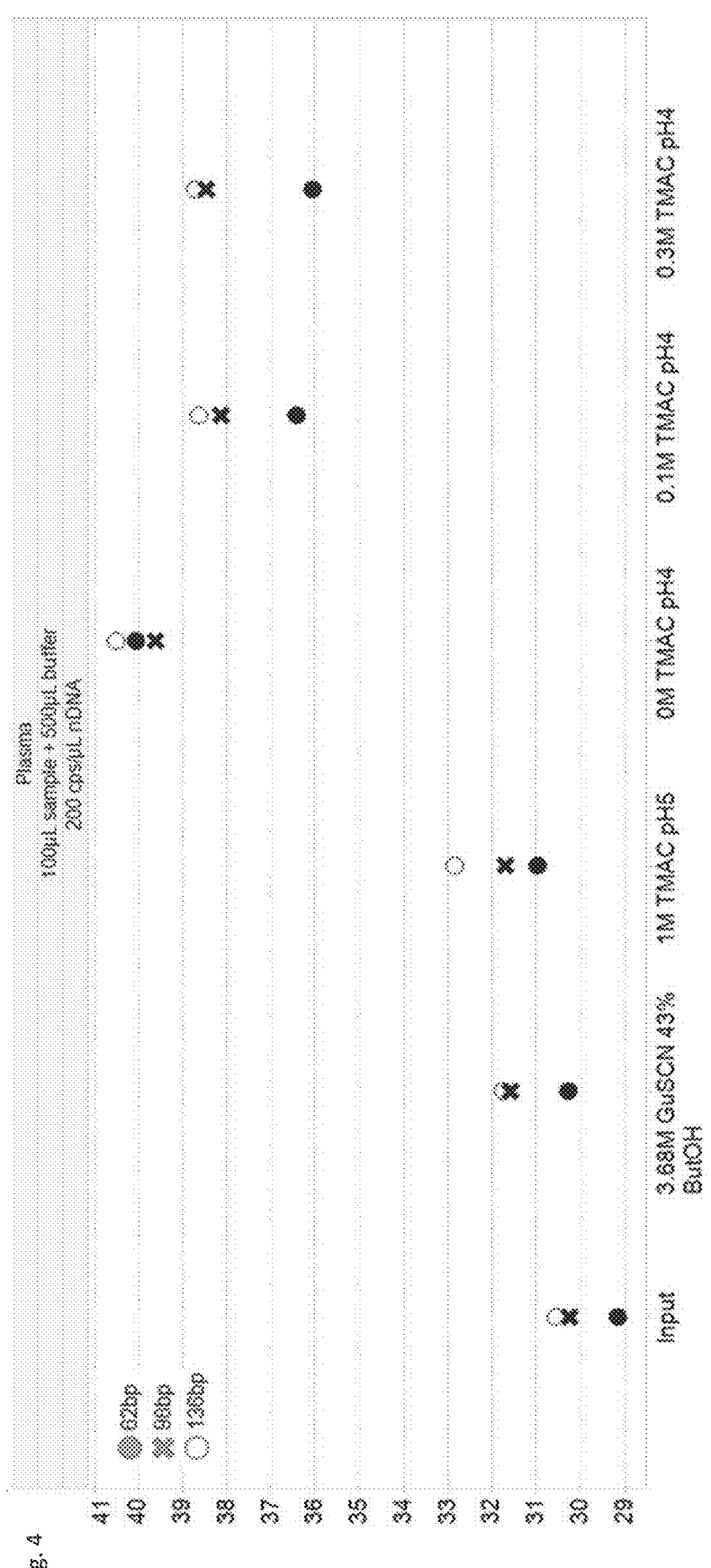
FIG. 4: shows comparison of different DNA extraction chemistries at different pH ranges.

We then investigated optimal pH ranges for plasma samples. The results are shown in FIG. 4. The Y-axis displays Ct values of all three different amplicon sizes. The X-axis displays different binding buffer compositions. This experiment shows that lowering the pH of the binding buffer to 4 is incompatible with native plasma samples. As soon as 0.3M of TMAC is added, protein aggregation becomes so severe that successful processing of the sample is nearly impossible. This is most likely related to the isoelectric point (pl) of the albumin abundant in plasma (4.7). As soon as the pH of the solution gets to close the pl of protein, the charge repulsion between the individual protein molecules is reduced and precipitation may occur. At this point, it appears that only a slight dehydrating effect by the anion is sufficient to promote protein aggregation.

Figure 5:
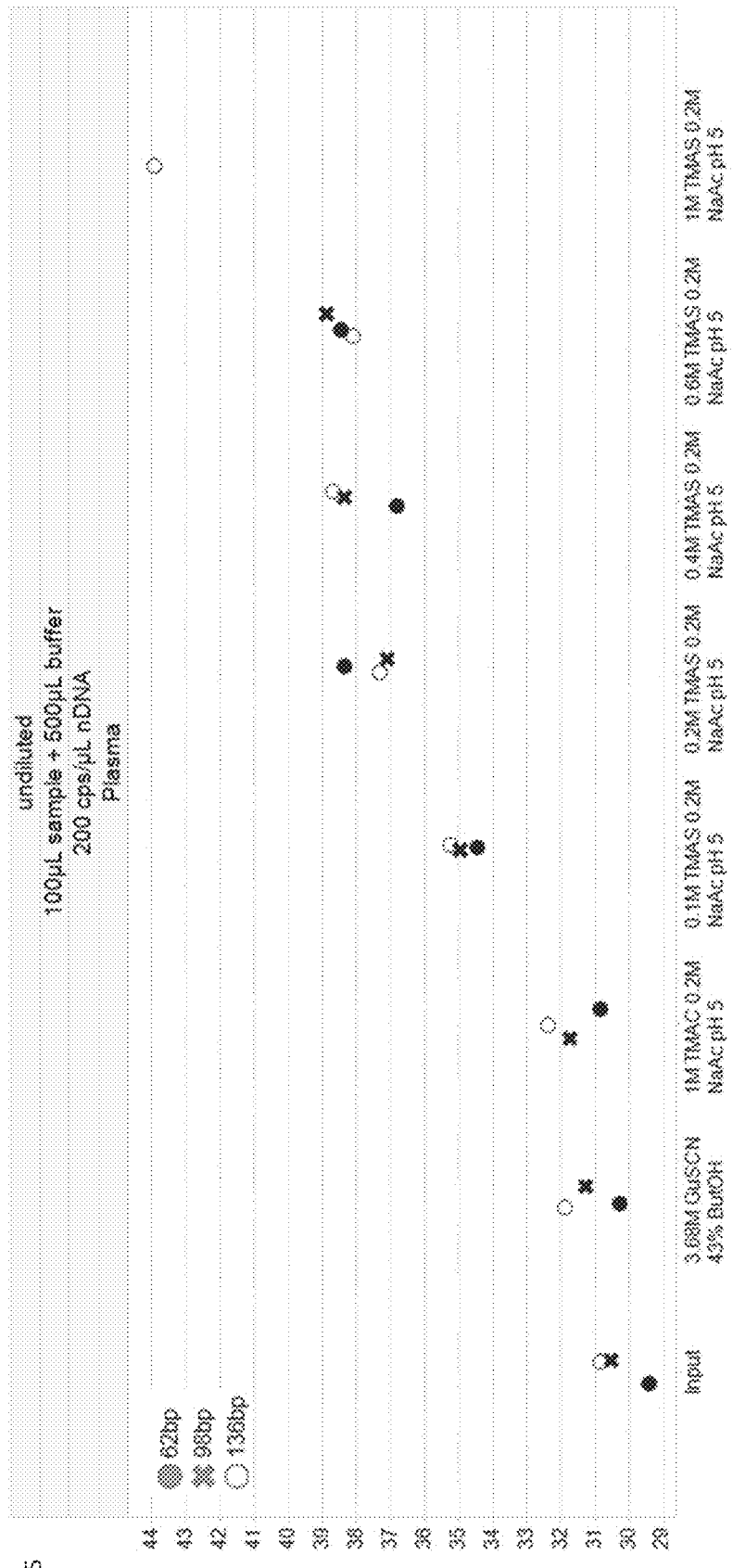
FIG. 5: shows comparison between TMAS and TMAC.

As a next step we have compared the performance of TMA sulphate (TMAS) vs TMAC, the results of which are shown in FIG. 5. The Y-axis displays Ct values of all three different amplicon sizes. The X-axis displays different binding buffer compositions. The experiment shows that TMAS does not efficiently mediate the binding of DNA to silica. The results were initially surprising based on our initial hypothesis, which assumed that the key relevant binding mechanisms were:

(i) dehydration of the silica membrane and the nucleic acid. Which is achieved by providing sufficient kosmotropic anions and thus reducing the amount of free water.

(ii) (ii) shielding of intermolecular electrostatic forces. Which is achieved by using acidic conditions and protonating the negatively charged silanol groups. Based on the above, we would have expected that sulphate, which due to its double charge is a stronger kosmotrope than chloride, would provide a stronger dehydrating effect and thus provide more efficient binding of DNA to silica. As confirmed in this and many other experiments, we concluded that other mechanisms must be in place than the above-described one. Melzak et al. (1996) have described a third effect that may have an impact on DNA-silica interaction, being (iii) the intermolecular hydrogen bond formation in the nucleic acid-silica contact layer. The data appears to suggest that these hydrogen bonds may be of greater importance than initially thought and that by using a strong kosmotropic sulphate anion the formation of these bonds is strongly perturbed or even prevented. Thus, it is possible that the performance of the chloride anion, which was notably described as a weak kosmotrope or a borderline komostrope/chaotrope, might be unique to its specific characteristics that result in its interaction with water being not stronger than the interaction of water with itself.

Figure 6:
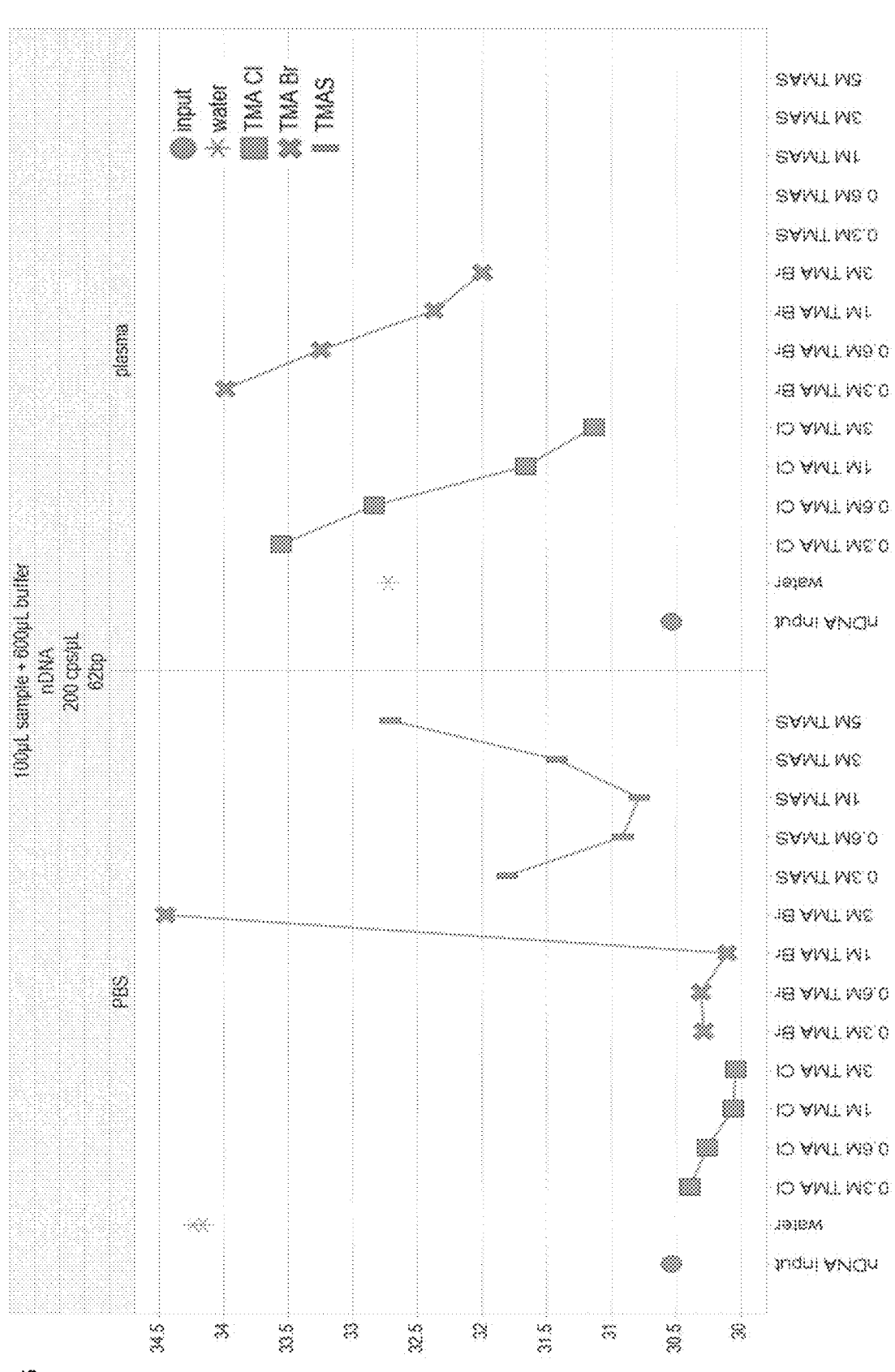
FIG. 6: shows performance of different TMA-containing salts.

To further investigate this hypothesis, we have compared the performance of different TMA-containing salts in mediating the binding of spiked nDNA to silica, in both PBS and plasma samples. The results are shown in FIG. 6. The Y-axis displays Ct values of the 62 bp amplicon. The X-axis displays different binding buffer compositions. The 'Input' shows a reference point and reflects the Ct values that are obtained when the total amount of spiked nDNA is targeted. Thus delta Ct with the reference point indicates extraction efficiency (i. e. a delta of 1 Ct=50% extraction efficiency). The data illustrates the importance of the selected anion. The charge density of the chloride enables the highest extraction efficiency at the lowest concentration. A more kosmotropic anion like sulphate, with a higher charge density, quickly reduces extraction efficiency, possibly by mediating B- to A-DNA conformational shifting or any other unknown mechanism. On the other hand, a more chaotropic anion like bromide, with a lower charge density, likely prevents such conformational shifting but is visibly less efficient in dehydrating the silica membrane and thus higher molarities are required to enable equal performance as conferred by the choice of chloride. It should also be noted that a reduced charge density of the more chaotropic anions also negative impacts the solubility of the quaternary ammonium salt. In this perspective, TMAC is superior both in performance and solubility.

Figure 7:
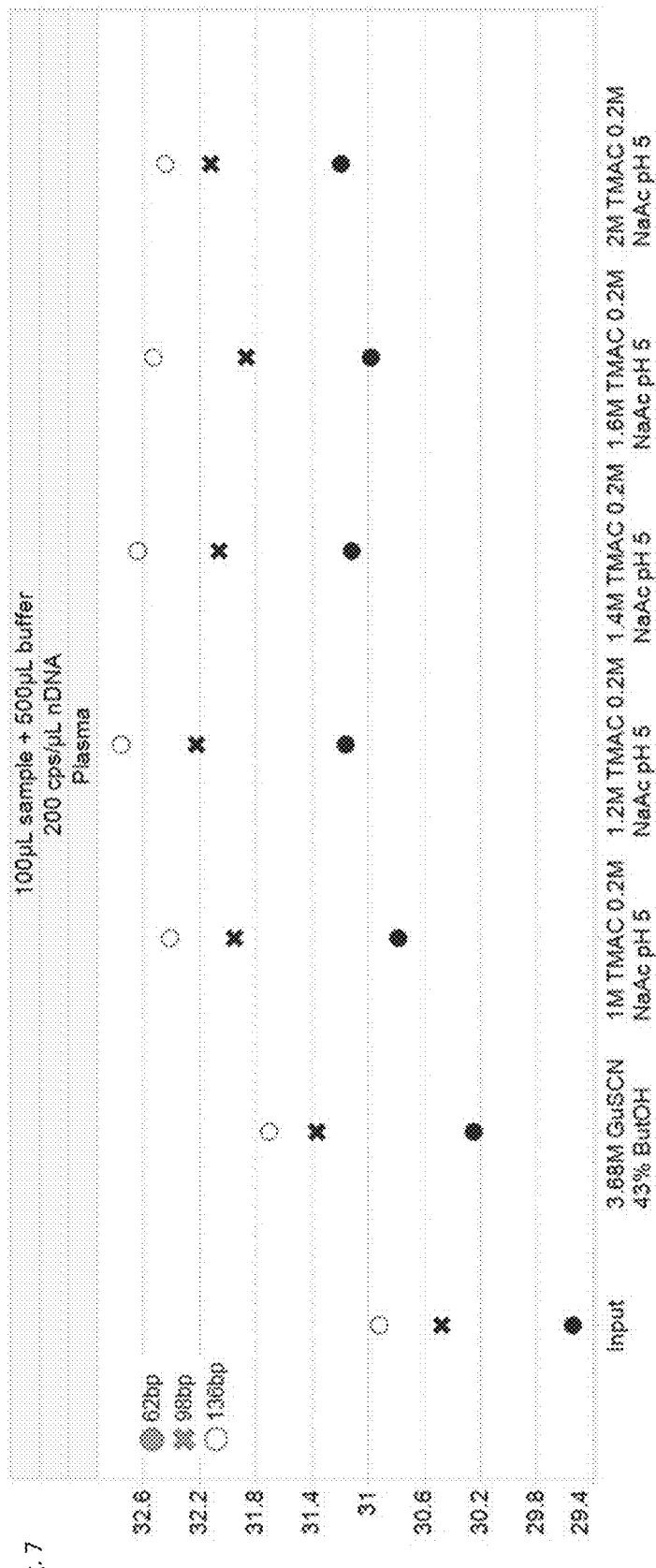
FIG. 7: shows performance of TMAC at different binding concentrations.
Figure 8:
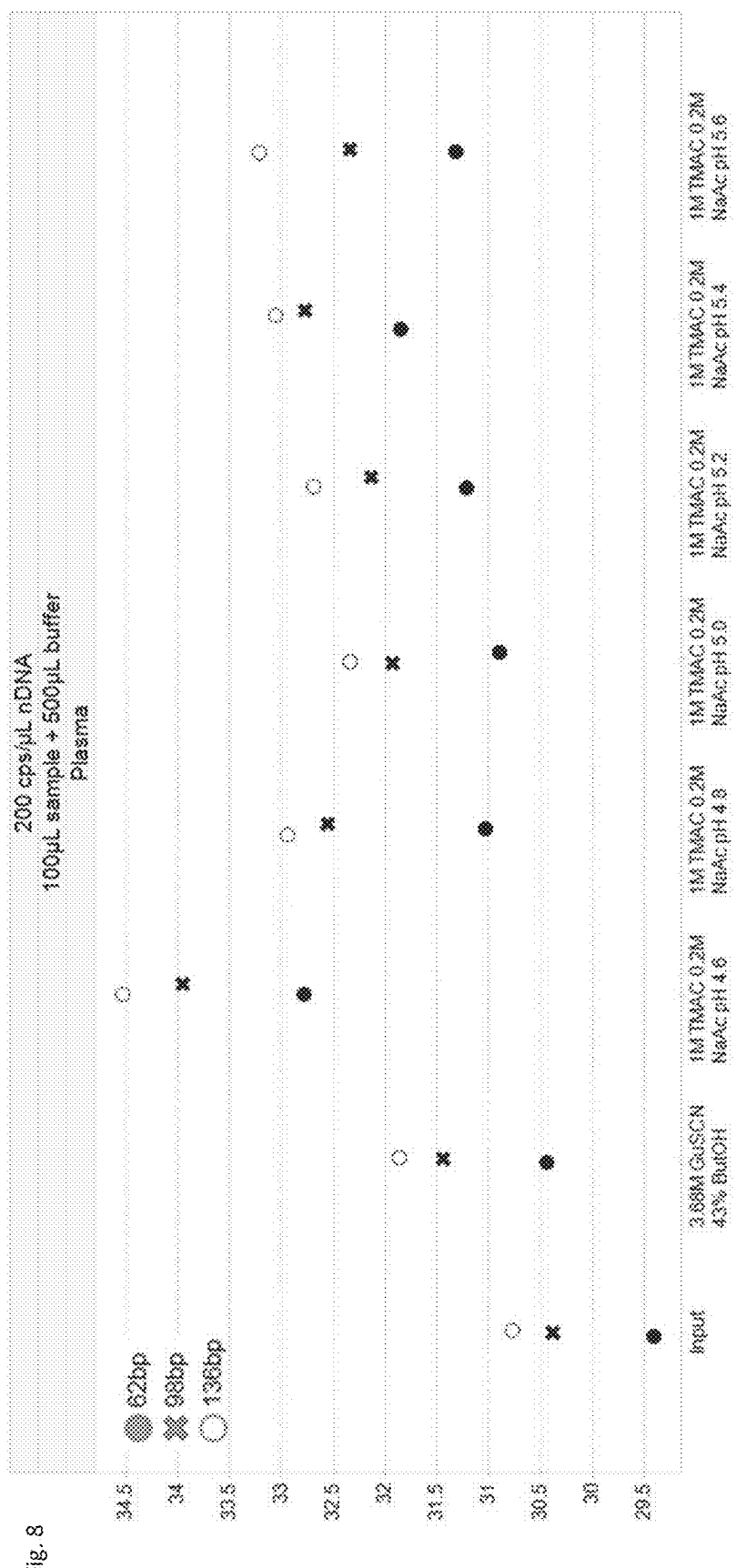
FIG. 8: shows performance of TMAC at different pH values.

Having confirmed that TMAC is the most promising quaternary ammonium salt, we have then investigated its optimal concentrations in our particular experimentation settings. The results are shown in FIG. 7. The Y-axis displays Ct values of all three different amplicon sizes. The X-axis displays different binding buffer compositions. The results show that increasing the concentration of TMAC in the binding buffer above 1M does not have a beneficial effect on the binding efficiency of DNA to silica. Binding efficiency is even slightly reduced when the concentration of TMAC is increased We then investigated dsDNA extraction performance using TMAC at different pH values. The results are shown in FIG. 8. The Y-axis displays Ct values of all three different amplicon sizes. The X axis displays different binding buffer compositions. The results show the importance of the pH of the binding buffer. As explained earlier, when processing undigested plasma, lowering the pH of the binding buffer near the isoelectric point of albumin (4.7) will cause severe protein aggregation, making it impossible to process the sample in a spin column or a microfluidic channel. Additionally, increasing the pH of the binding buffer above five slightly increases the negative charge repulsion between the silanol groups and the phosphate backbone of DNA, which results in reduced binding efficiency of DNA to silica. The surface silanol groups on the silica membrane have been described to have pKa values ranging from four to eight. Increasing the pH likely causes deprotonation of silanol groups with the lowest pKa values, thus making them negatively charged.

Figure 9:
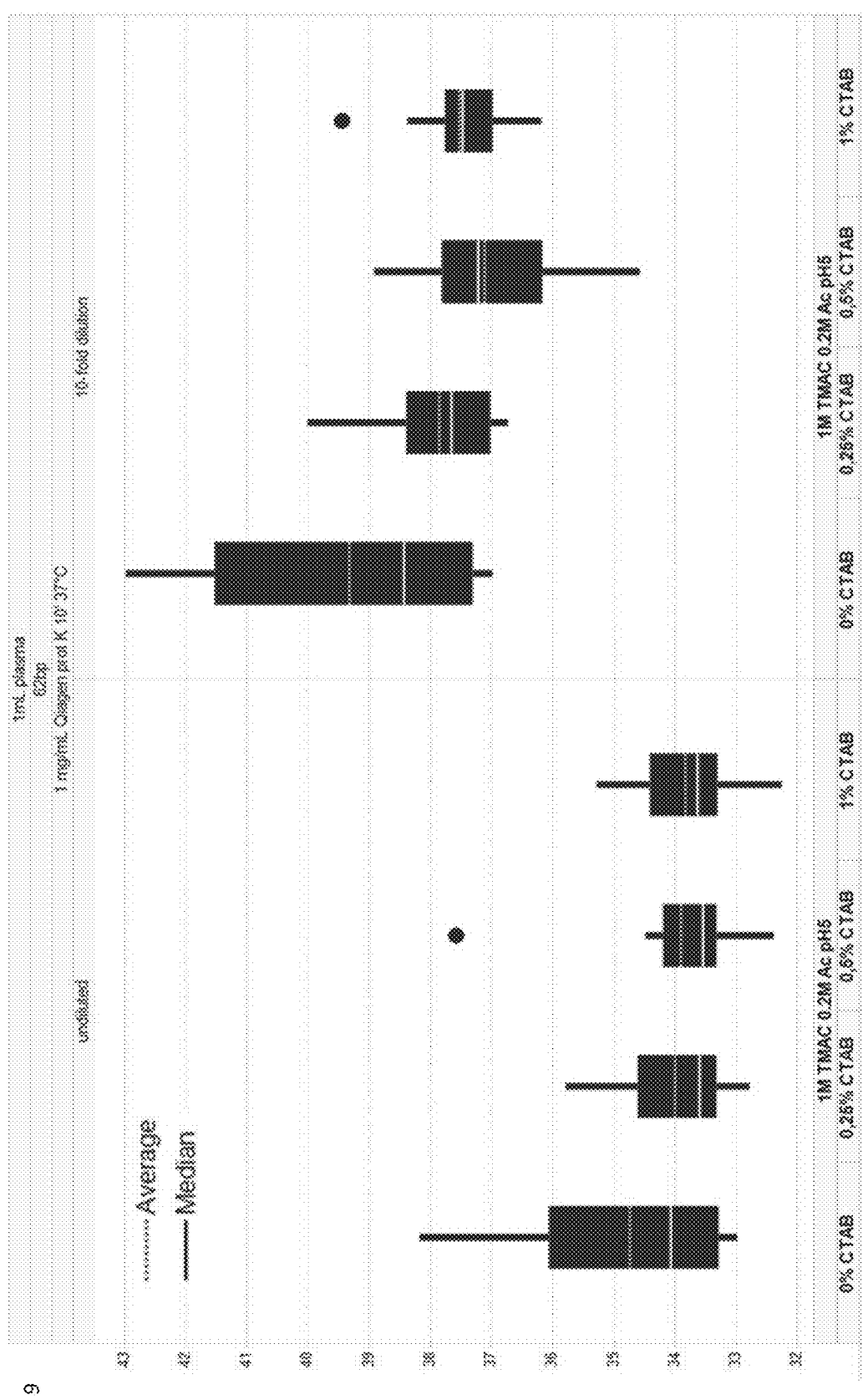
FIG. 9: shows performance of TMAC on different plasma batches with or without CTAB at different concentrations.

We then have studied the molarity of TMAC and the pH of the acetate buffer in a more extensive manner for multiple and different batches of plasma. Additionally, we have also added a quaternary ammonium detergent cetyltrimethylammonium bromide (CTAB) to the binding buffer. The results are shown in FIG. 9. The Y-axis displays Cq values of the 62 bp amplicon. The X-axis shows the binding conditions, including different amounts of added CTAB. Unlike previous experiments, where a limited amount of plasma was processed after spiking it with nDNA, this experiment focusses on the extraction of cfDNA from 1 ml unspiked plasma. For an additionally improved effect, the plasma samples were also subjected to a 10-minute protein digestion step at 37° C., using 1 mg/ml of proteinase K. 1 ml plasma samples where processed by adding 0.75 ml of binding buffer (2.33 MTMAC 0. 47M Acetate 1.17% CTAB pH 5). Subsequently, the membrane was washed with 1 ml of a first washing buffer (1 M TMAC 0.2 M Acetate pH 5), finally washing the membrane with an additional 1 ml of 90% EtOH. For each binding condition, 10 different samples were processed. The boxplot in FIG. 9 shows the average and median Cq values, as well as the variation. It is clear that the addition of CTAB can have a beneficial effect as it can reduce sample-to-sample variability and increase DNA yield. We think that this effect is caused by CTAB promoting the solubility of albumin, and thus preventing it from precipitating on the silica membrane. It likely also inhibits nuclease activity and possibly as well assists in the removal of cfDNA from histones.

Figure 10:
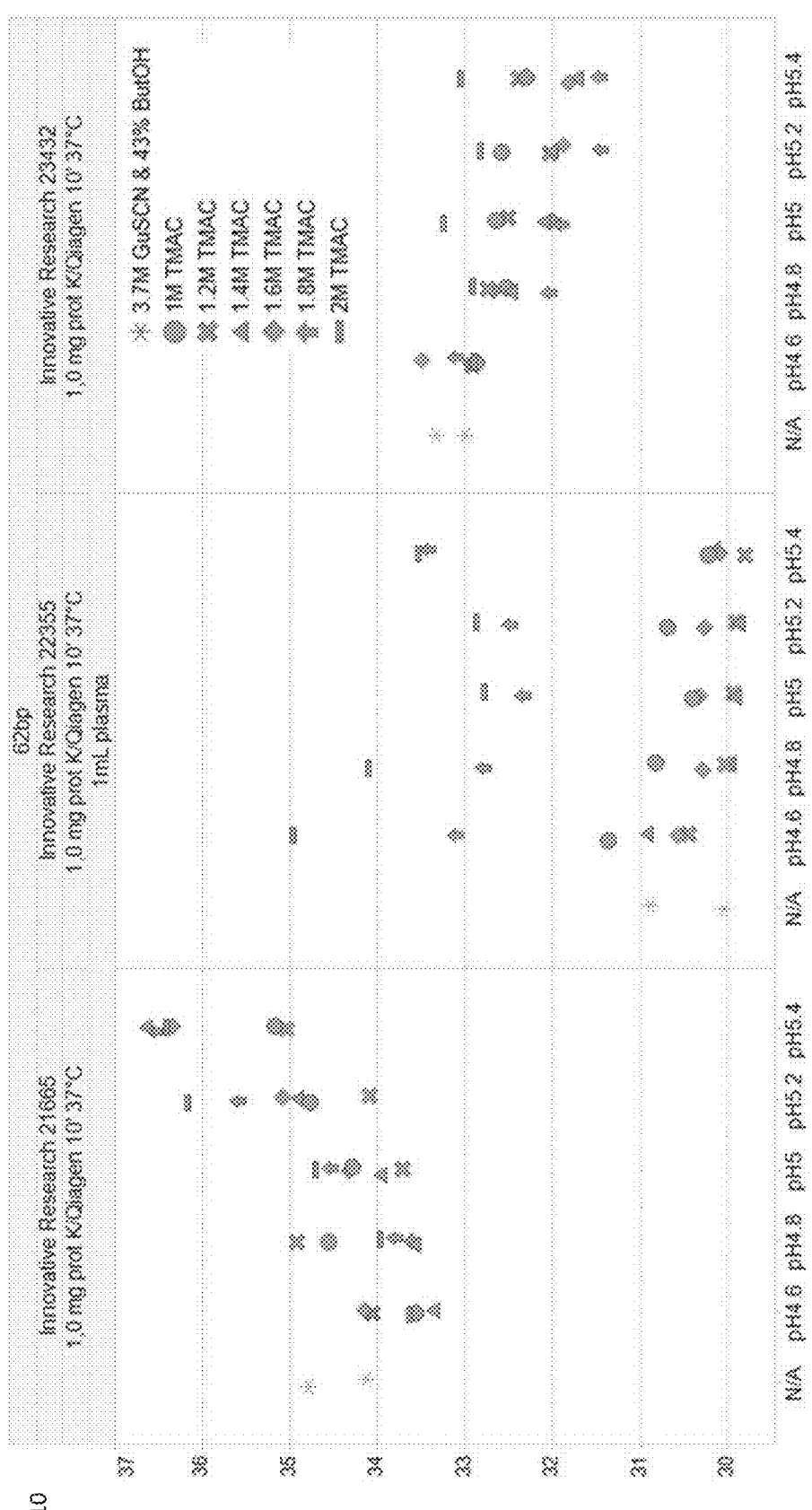
FIG. 10: shows performance of different TMAC buffers.

Then, we looked at different TMAC molarities at different pH values. By evaluating different binding conditions for multiple batches of plasma, it became apparent that different samples respond very differently to the different conditions as shown in FIG. 10. The Y-axis shows Ct values of the 62 bp amplicon. The X-axis displays the different pH values of the binding conditions. The shape of the plots represent the different TMAC molarities (as explained in the legend).

Figure 11:
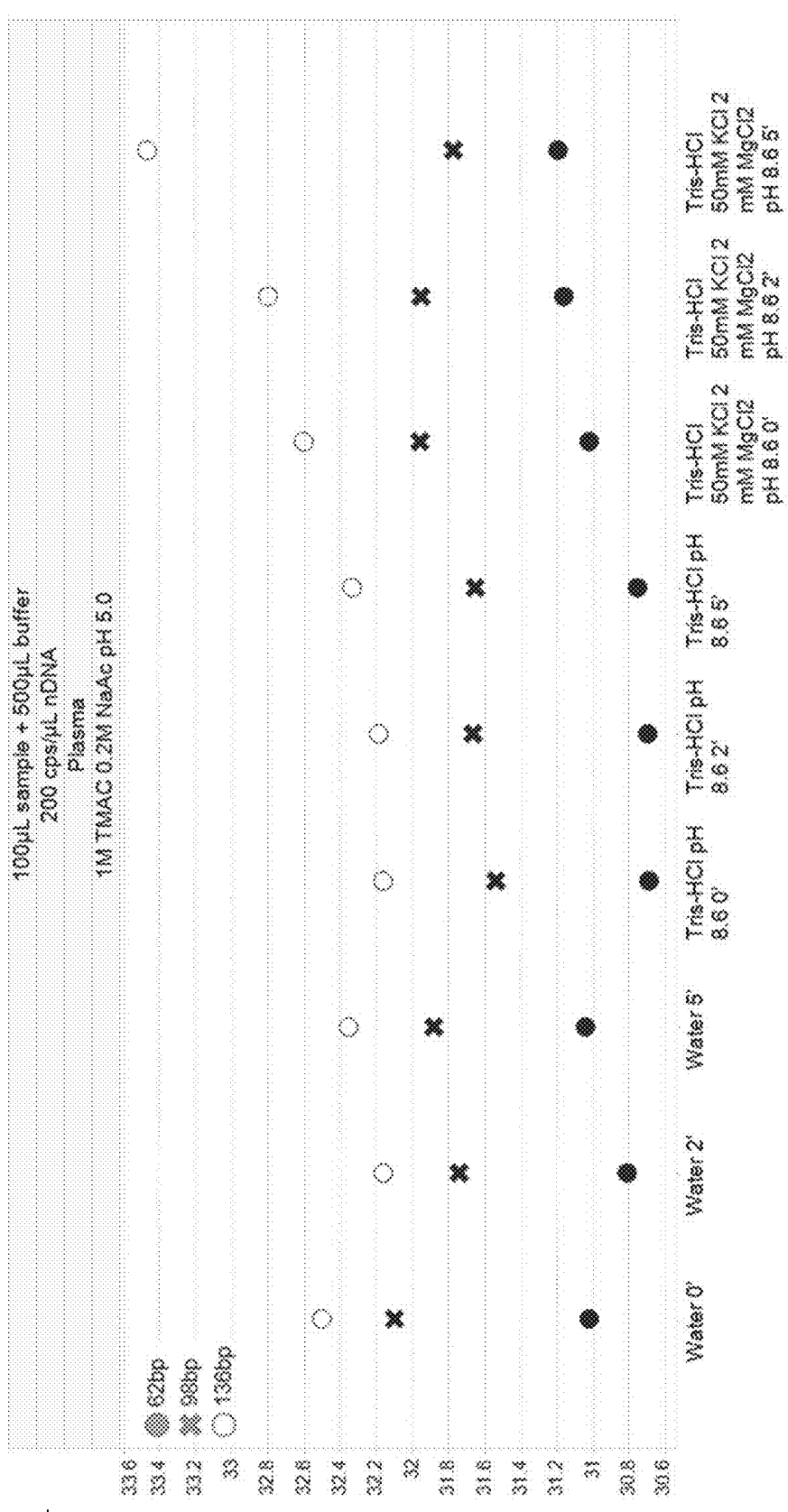
FIG. 11: shows investigation of different elution conditions.

We then investigated efficiency of elution conditions. The results are shown in FIG. 11. The Y-axis shows Ct values for all three different amplicon sizes. The X-axis shows different elution buffer compositions and incubation times at room temperature. The data shows that the elution step is most efficient when a slightly basic buffer is used. Again, this is possibly related to the pKa values of the surface silanol groups. We think that the negative charge repulsion between the silanol groups and the phosphate backbone is the main driving force during elution, accompanied by rehydration. Consequently, providing an elution buffer with a pH>the highest silanol pKa value (8), will ensure that all silanol groups are negatively charged. From FIG. 11, it can be seen that the presence of 50 mM K+ and 2 mM Mg++ negatively impacts elution efficiency. We hypothesize that this effect may possibly be caused by these strong kosmotropic cations shielding the negative charge repulsion between the silanol groups and the phosphate backbone. This observation should be borne in mind when adapting the protocol to fully integrated molecular diagnostic devices where silica-bound nucleic acids are eluted directly with an amplification buffer.

Figure 12:
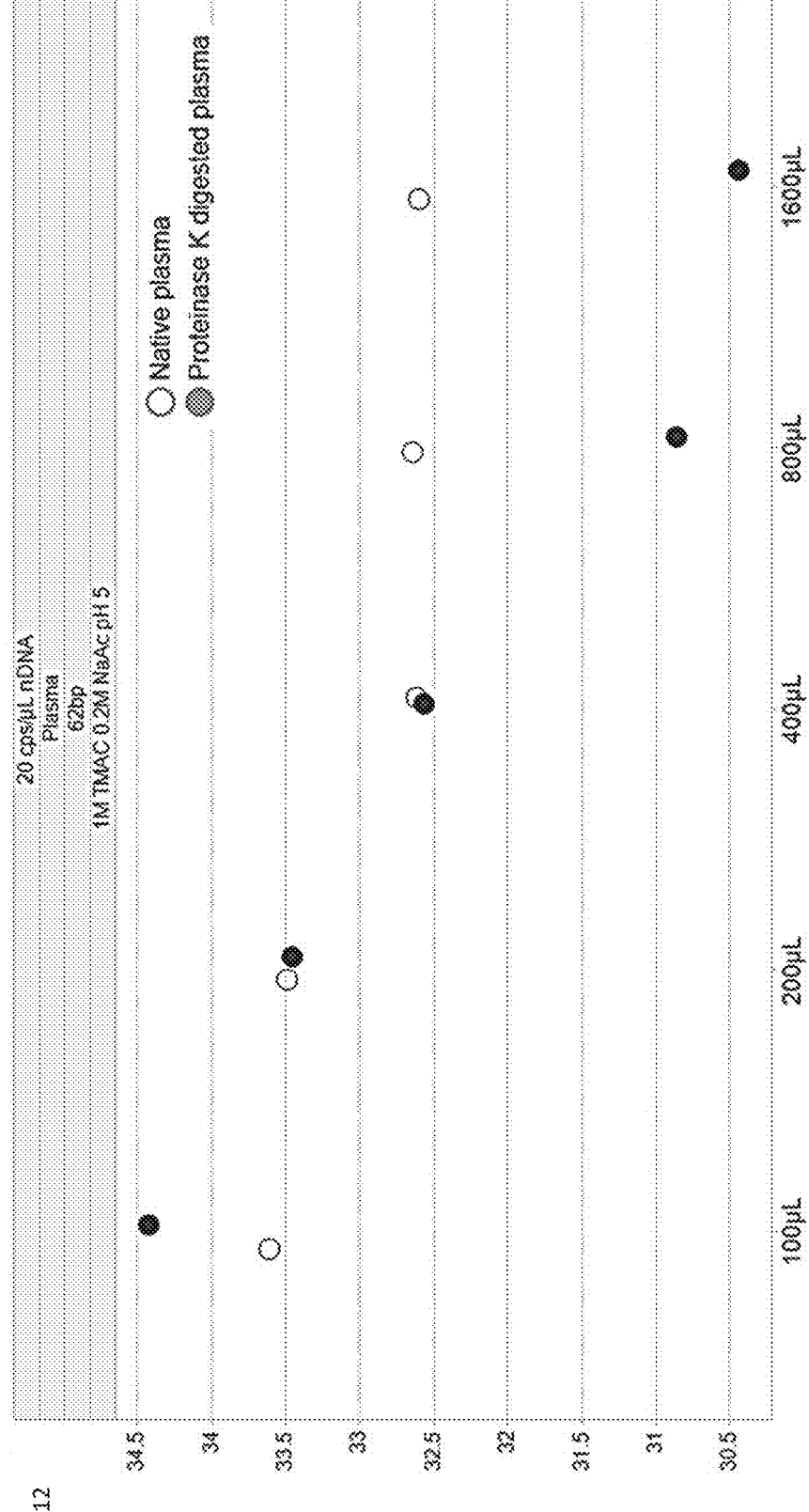
FIG. 12: shows potential benefits of including proteinase pre-digestion.

Next, we investigated potential beneficial effects of incorporation of Proteinase K pre digestion, in particular for difficult plasma samples, in function of the volume of the starting material. The results are shown in FIG. 12. The Y-axis displays Ct values of the 62 bp amplicon. The X-axis shows the different plasma volumes that were processed. The results illustrate that the incorporation of a proteinase K digestion step increases DNA yield when processing plasma samples>400 μL. Plasma was digested for 10 minutes at 56° C. We suspect that binding of proteins to the silica membrane also happens to certain extend under the binding buffer chemistry as investigated herein. The acidic conditions reduce the negative charge of albumin that has pl=4.7, which significantly reduces charge repulsion between this abundant plasma protein and the silica membrane. Consequently, proteins and nucleic acids are expected to compete for binding sites, while the surface of the silica membrane remains limited. Additionally, reduced charge repulsion between the individual protein molecules enables them to stack much closer together when binding to the membrane. Hence, the digestion or removal of albumin from plasma is likely to be beneficial for improving binding of nucleic acids to the silica membrane when processing larger samples.

Figure 13:
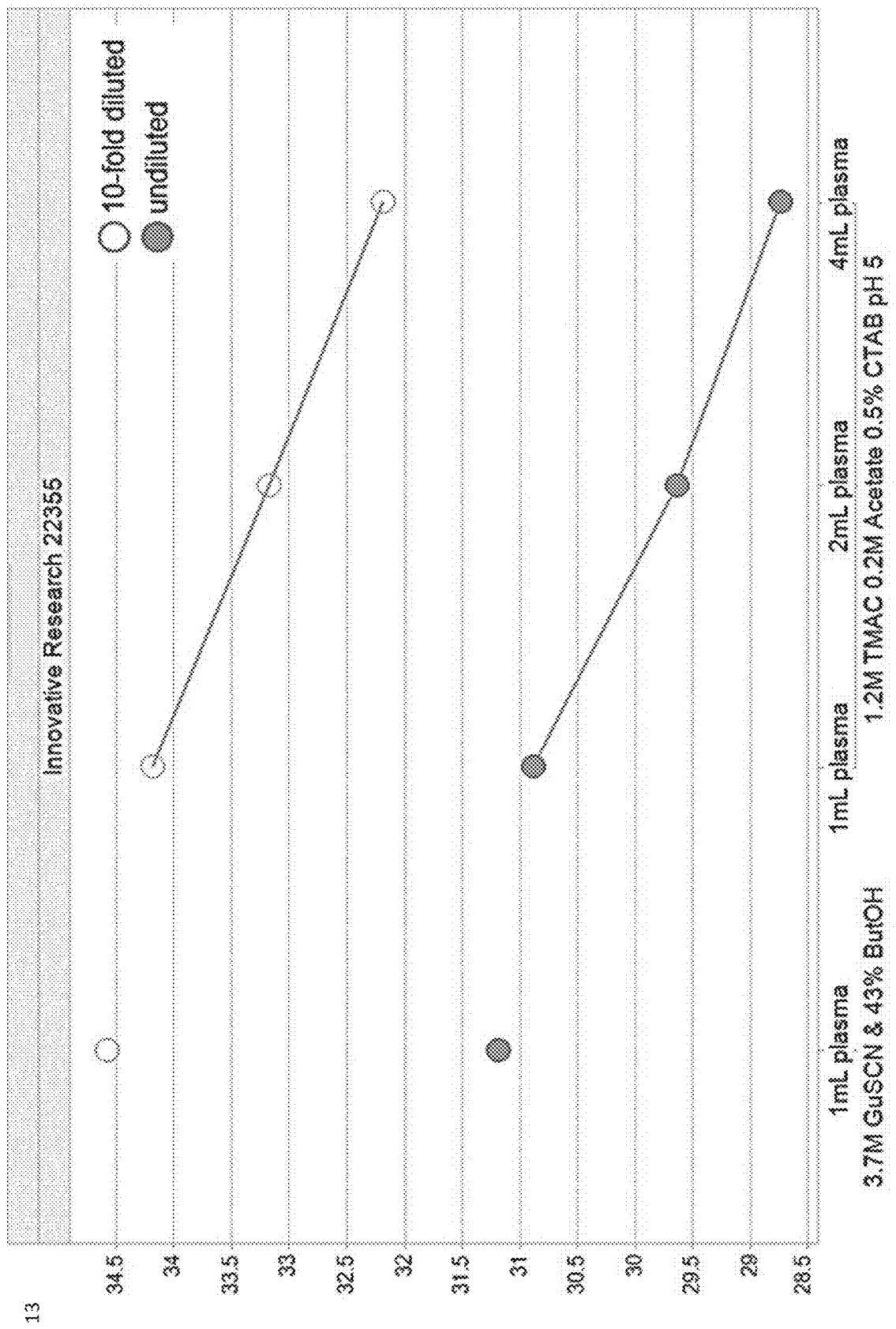
FIG. 13: shows the performance of the method in a closed integrated cartridge.

We then evaluated plasma sample volume upscaling in the disposable proprietary to Biocartis NV cartridge belonging to the Ldylla™ integrated system. The results are shown in FIG. 13. The Y-axis displays Ct values of the 62 bp amplicon. The X-axis displays the different plasma volumes that were processed, using different binding buffer chemistries. The samples used were unspiked plasma samples. The results promisingly show that the presented herein novel binding buffer chemistry allows substantial sample upscaling in the ldylla cartridge, which results in a linear yield gain. The binding conditions applied were the following:

1.2M TMAC 0.2M acetate 0.5% CTAB pH 5. The final buffer layout as used in the cartridge-based was the following:

Binding buffer (3 ml): 2.8M TMAC 0.47M acetate 1.17% CTAB pH 5 (diluted 2.33 times with the sample)

Plasma sample (4 ml) (treated with 1 mg/ml of proteinase K for 10' at room temperature)

$1^{st}$ washing buffer (1.25 ml): 1.2M TMAC 0.2M acetate pH 5

$2^{nd}$ washing buffer (2.4 ml): 90% ethanol

Elution buffer: H2O (scalable volume to whatever the needs are, for Idylla the minimal elution volume is 160 μL. Maximal elution volume is 250 μL)

Figure 14:
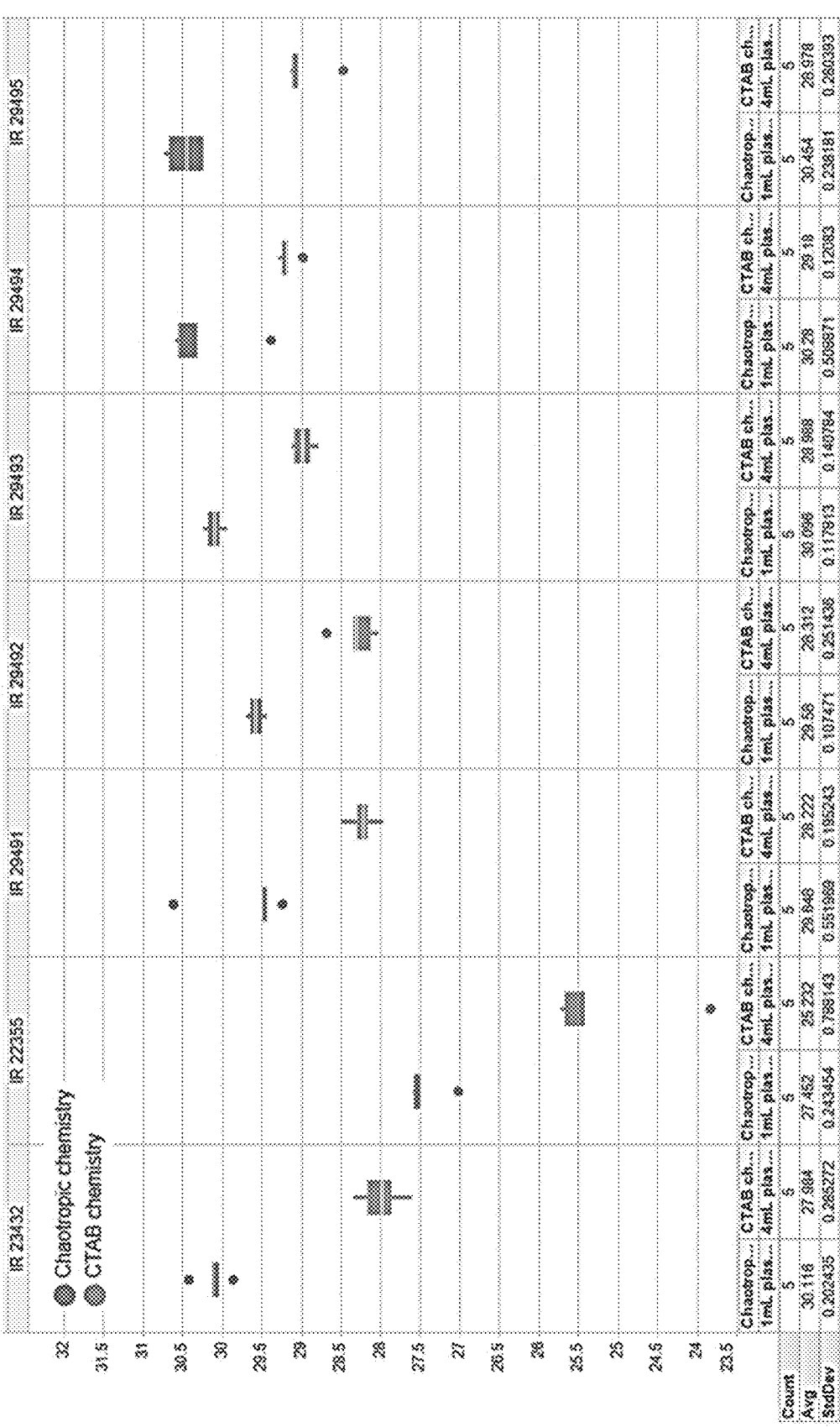
FIGS. 14 and 15: show comparison between Boom-extraction and TMAC+CTAB extraction chemistries on different plasma batches in closed integrated cartridges.
Figure 15:
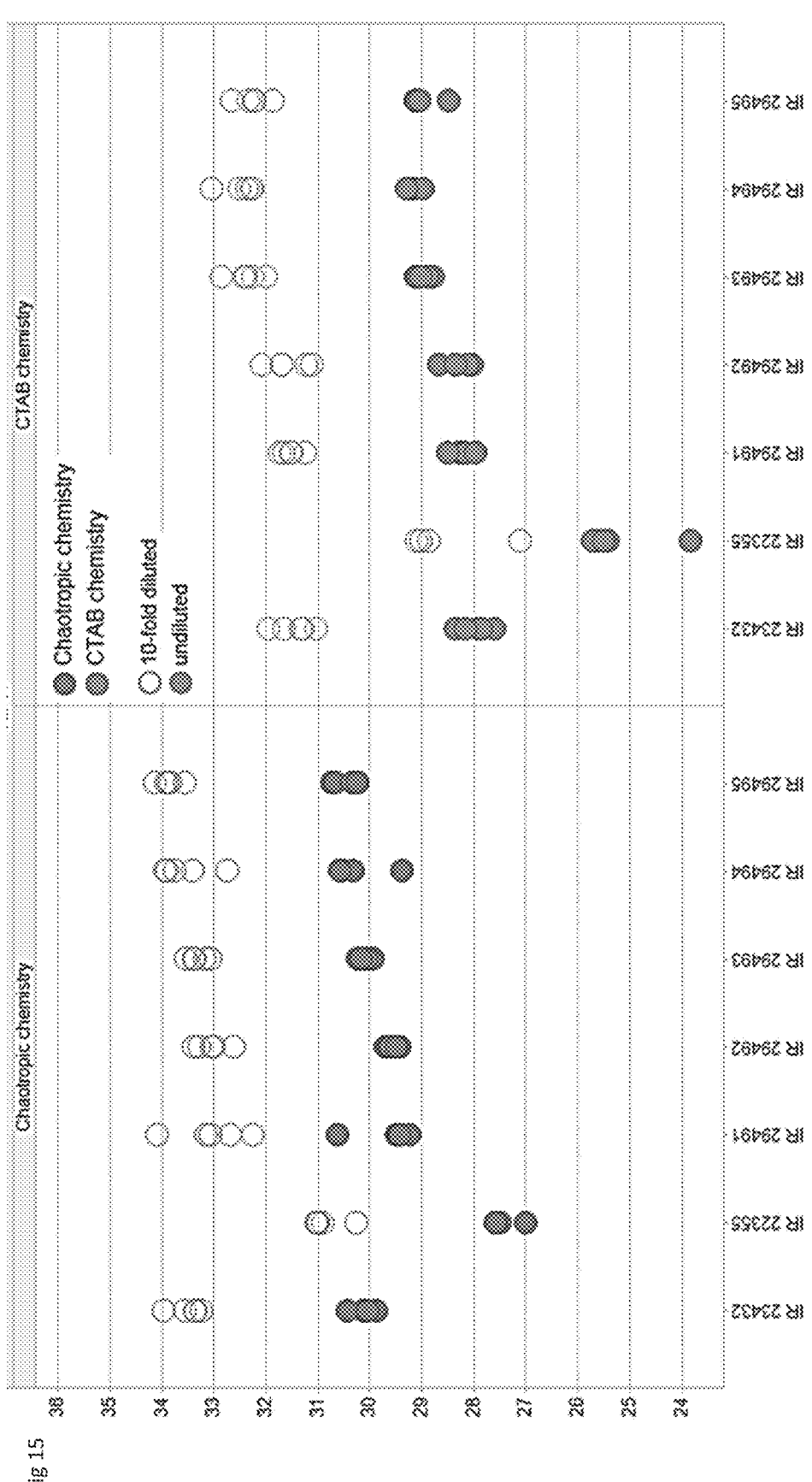

Lastly, we decided to compare performance of cartridges using the disclosed novel extraction chemistry with the chaotropic reference chemistry. To do so, we used seven different plasma batches, and ran five cartridge repeats per batch for each extraction chemistry. All runs of the 70 cartridges were successfully completed without any clogging errors. The results are shown in FIGS. 14 and 15. In FIG. 14 the Y-axis shows Ct values of a 62 bp target amplicon. The X-axis specifies the extraction chemistries (chaotropic reference on the left-hand side and the novel TMAC+CTAB chemistry on the right-hand side per each panel) and sample volumes (1 ml and 4 ml, respectively). Each panel represents a different batch of plasma. In FIG. 15, the Y-axis shows Ct values for the same amplicon, while the X-axis lists the different batches of plasma. Each panel represents a different extraction chemistry (chaotropic reference on the left-hand side and the novel TMAC+CTAB chemistry on the right-hand side). The empty dots are 10-fold dilutions of the full dots, and are thus indicative of PCR inhibition. The data of FIGS. 14 and 15 show that the increased sample input (4 ml), enabled by the use of the novel extraction chemistry, results in substantial yield gain. The actual measured yield increases are listed in Table 1 below. FIG. 15 additionally shows that none of the sample extracts contained any PCR-inhibitory components. The results show that the novel binding chemistry is robust with standard deviations comparable to those of the chaotropic reference chemistry. Furthermore, for all of the studied plasma batches, at least a 2-fold yield gain was obtained thanks to the ability to increase the sample input volume per cartridge, in as shown in Table 1. Apart from this increased assay sensitivity, it should be noted that the novel buffer chemistry is completely chaotrope-free and low-cost.

TABLE 1

| | | | |
|---|---|---|---|
| Average Ct values obtained for each batch of plasma in FIG. 14. The delta Ct between both extraction chemistries reflects the cfDNA yield gain. | | | |
| Plasma batch | Chaotropic chemistry - 1 mL (Average Ct) | CTAB chemistry - 4 mL (Average Ct) | Delta Ct |
| IR 23432 | 30.166 | 27.984 | 2.182 |
| IR 22355 | 27.452 | 25.232 | 2.22 |
| IR 29491 | 29.648 | 28.222 | 1.426 |
| IR 29492 | 29.58 | 28.312 | 1.268 |
| IR 29493 | 30.096 | 28.988 | 1.108 |
| IR 29494 | 30.28 | 29.18 | 1.1 |
| IR 29495 | 30.454 | 28.978 | 1.476 |

I claim:

1. A double-stranded DNA (dsDNA) extraction method comprising contacting a liquid biopsy sample with a silica solid support at pH value between 3 and 6 and in the presence of a salt consisting of:

a small quaternary organic compound, defined as a quaternary compound consisting of a central positively charged atom with four organic substituents (R1, R2, R3, and R4), wherein the number of carbon atoms in each organic substituent (R1, R2, R3, and R4) does not exceed 2; and a bromide or a chloride anion to extract dsDNA of 10 to 300 base pairs;

wherein the central positively charged atom of the small quaternary organic compound is nitrogen, and wherein the concentration of the small quaternary organic compound is 0.1 M-2 M.

2. The method according to claim 1, wherein the anion is chloride.

3. The method according to claim 2, wherein the small quaternary organic compound is tetramethylammonium chloride (TMAC).

4. The method according to claim 1, wherein the concentration of the small quaternary organic compound is 0.5 M-1.8 M.

5. The method according to claim 1, wherein the pH value is 4-5.8.

6. The method according to claim 1, wherein the contacting with the silica solid support is preceded by a protease treatment.

7. The method according to claim 1, wherein the liquid biopsy sample is selected from plasma, serum, whole blood, or urine.

8. The method according to claim 1, wherein the dsDNA is cell free dsDNA.

9. The method according to claim 1, wherein the dsDNA is circulating tumor dsDNA.

10. The method according to claim 1, wherein the contacting is further in the presence of a detergent.

11. The method according claim 10, wherein the detergent is a quaternary ammonium compound detergent.

12. The method according claim 11, wherein the quaternary ammonium compound detergent is cetyltrimethylammonium bromide (CTAB).

13. The method according to claim 1, wherein the method is performed using a cartridge.

14. The method according to claim 1, wherein the concentration of the small quaternary organic compound is about 1.2 M.

15. The method according to claim 1, wherein the pH value is 4.2-5.6.

16. The method according to claim 1, wherein the pH value is 4.4-5.4.

17. The method according to claim 1, wherein the pH value is about 5.

* * * * *